(12) United States Patent
Martone et al.

(10) Patent No.: US 7,056,284 B2
(45) Date of Patent: Jun. 6, 2006

(54) ENDOSCOPE ASSEMBLIES HAVING WORKING CHANNELS WITH REDUCED BENDING AND STRETCHING RESISTANCE

(75) Inventors: Stephen Martone, Westford, MA (US); Katsumi Oneda, Alpine, NJ (US)

(73) Assignee: Vision Sciences, Inc., Natick, MA (US)

( * ) Notice: Subject to any disclaimer, the term of this patent is extended or adjusted under 35 U.S.C. 154(b) by 39 days.

(21) Appl. No.: 10/821,036

(22) Filed: Apr. 7, 2004

(65) Prior Publication Data

US 2004/0193007 A1    Sep. 30, 2004

Related U.S. Application Data

(62) Division of application No. 10/040,972, filed on Jan. 4, 2002, now Pat. No. 6,740,030.

(51) Int. Cl.
*A61B 1/00* (2006.01)
(52) U.S. Cl. .................. 600/123; 600/121; 600/153
(58) Field of Classification Search ........ 600/121–125, 600/104, 139, 146, 153
See application file for complete search history.

(56) References Cited

U.S. PATENT DOCUMENTS

| | | | | |
|---|---|---|---|---|
| 4,353,358 A | 10/1982 | Emerson | .......... | 128/4 |
| 4,580,551 A | 4/1986 | Siegmund et al. | .......... | 128/4 |
| 4,651,753 A | 3/1987 | Lifton | .......... | 128/751 |
| 4,653,476 A | 3/1987 | Bonnet | .......... | 128/4 |
| 4,669,172 A | 6/1987 | Petruzzi | .......... | 29/456 |
| 4,714,075 A | 12/1987 | Krauter et al. | .......... | 128/4 |
| 5,025,778 A | 6/1991 | Silverstein | .......... | 128/4 |
| 5,259,366 A | 11/1993 | Reydel et al. | .......... | 600/124 |
| 5,417,697 A | 5/1995 | Wilk et al. | .......... | 606/113 |
| 5,483,951 A | 1/1996 | Frassica et al. | .......... | 600/104 |
| 5,503,616 A | 4/1996 | Jones | .......... | 600/155 |
| 5,741,271 A | 4/1998 | Nakao et al. | .......... | 606/114 |
| 5,749,889 A | 5/1998 | Bacich et al. | .......... | 606/198 |
| 5,820,630 A | 10/1998 | Lind | .......... | 606/208 |
| 5,827,177 A | 10/1998 | Oneda et al. | .......... | 600/121 |
| 5,931,833 A | 8/1999 | Silverstein | .......... | 606/1 |
| 6,071,233 A | 6/2000 | Ishikawa et al. | .......... | 600/104 |
| 6,309,346 B1 | 10/2001 | Farhadi | .......... | 600/114 |
| 6,585,642 B1 * | 7/2003 | Christopher | .......... | 600/156 |

* cited by examiner

*Primary Examiner*—Beverly M. Flanagan
(74) *Attorney, Agent, or Firm*—Dorsey & Whitney LLP

(57) ABSTRACT

Apparatus and methods for endoscope assemblies having working channels with reduced bending and stretching resistance are disclosed. In one embodiment, an endoscope assembly includes a sheath having a body portion adapted to at least partially encapsulate an endoscopic insertion tube, and a working channel attached to the body portion and extending along at least a portion of the body portion. The working channel includes a component for reducing the resistance of the assembly to bending and stretching. In alternate aspects, the working channel may include a cut, a gap, a sliding portion, or an expansion section. Endoscope assemblies having a working channel in accordance with the invention advantageously reduce the articulation and stretching resistance of the assembly during articulation of the endoscope assembly. Also, because the axial forces (tension and compression) within the working channel are reduced, the working channel can be fabricated out of a relatively hard, inelastic material, thereby reducing the friction within the working channel and improving the physician's ability to perform a medical procedure.

94 Claims, 15 Drawing Sheets

ENDOSCOPE ASSEMBLIES HAVING WORKING CHANNELS WITH REDUCED BENDING AND STRETCHING RESISTANCE

CROSS-REFERENCE TO RELATED APPLICATION

This application is a divisional of U.S. patent application Ser. No. 10/040,972, filed Jan. 4, 2002 now U.S. Pat. No. 6,740,030.

TECHNICAL FIELD

The present invention is directed toward endoscopic apparatus and methods, and more specifically, to endoscope assemblies having working channels with reduced bending and stretching resistance.

BACKGROUND OF THE INVENTION

Endoscopes are widely used for a variety of medical procedures. To improve their performance, endoscopes have been optimized in various ways to best accomplish their purpose. Examples of specialized endoscopes include angioscopes, colonoscopes, bronchoscopes, and arthroscopes.

One of the medical procedures that may be performed using an endoscope is obtaining a biopsy sample. FIG. 1 shows a conventional endoscope assembly 10 used for obtaining a biopsy sample. The endoscope assembly 10 includes an endoscope 20 having an elongated insertion tube 22. The insertion tube 22 may be rigid, partially flexible, or entirely flexible The insertion tube 22 includes a distal portion 24 that may be inserted into a body cavity of a patient (not shown), and a working end 26.

The endoscope 20 includes a headpiece 28 that remains external to the patient during a medical procedure. In the embodiment shown in FIG. 1, the headpiece 28 includes an eyepiece 30 for viewing the scene through a viewing lens 31 at the working end 26 of the insertion tube 22, a pair of articulation control knobs 32 for manipulating the position of the distal portion 24 of the insertion tube 22, and a pair of fluid control actuators 34 for controlling the flow of fluids through tubes 36 to (or from) the working end 26. Endoscopes 20 of the type generally shown in FIG. 1 are described more fully, for example, in U.S. Pat. No. 5,931,833 issued to Silverstein, U.S. Pat. No. 5,483,951 issued to Frassica and Ailinger, and U.S. Pat. No. 4,714,075 issued to Krauter and Vivenzio, which patents are incorporated herein by reference. Representative commercially-available endoscopes include, for example, video or fiberoptically-equipped sigmoidoscopes, bronchoscopes, nasopharyngolaryngoscopes, colonoseopes, and gastroscopes.

As further shown in FIG. 1, the endoscope assembly 10 includes a sheath 40 that encapsulates the insertion tube 22 to prevent at least part of the insertion tube 22 from being soiled during the medical procedure. The sheath 40 may be flexible to allow unrestricted bending of the flexible portion of the insertion tube 22, or may be relatively rigid. In the depicted embodiment, the sheath 40 includes an enlarged fitting portion 42 that fits over an engagement portion 44 of the headpiece 28, and a working channel 46 having a proximal end 48 that projects outwardly from the sheath 40 proximate the headpiece 28.

FIG. 2 is an enlarged isometric view of the working end 26 of the endoscope assembly 10 of FIG. 1. As shown in FIG. 2, the sheath 40 surrounds the insertion tube 22 of the endoscope 20, and the working channel 46 extends along an outer surface of the insertion tube 22. The working channel 46 terminates in an open distal end 49 at the working end 26 of the insertion tube 22. A medical instrument 50, including a biopsy sampling device 52, extends through the working channel 46 (see FIG. 1) and projects from the open distal end 49 of the working channel 46. Sheaths of the type shown in FIGS. 1 and 2 are described more fully, for example, in U.S. Pat. No. 5,025,778 issued to Silverstein et al., U.S. Pat. No. 5,483,951 issued to Frassica et al., and U.S. Pat. No. 5,827,177 issued to Oneda et al.

During a medical procedure, the medical instrument 50 is inserted into the proximal end 48 of the working channel 46 and slid through the working channel 46 until the biopsy sampling device 52 emerges from the open distal end 49 at the working end 26. Through the eyepiece 30, the physician observes the biopsy sampling device 52 through the viewing lens 31 and manipulates the medical instrument 50 into the desired position and collects the desired sample. After a biopsy sample is obtained, the biopsy sampling device 52 containing the biopsy sample may be withdrawn through the working channel 46, or alternately, the entire insertion tube 22 may be withdrawn from the patient's body with the biopsy sampling device 52 remaining in position near the working end 26.

Although desirable results have been achieved using the conventional devices described above, some drawbacks do exist. For example, during a medical procedure, the flexible insertion tube 22 is generally manipulated into various bending positions using the articulation control knobs 32. It is therefore desirable for such endoscope assemblies that the sheath 40, including the working channel 46, be fabricated of a flexible material to allow for bending and articulation of the insertion tube 22. Furthermore, it may be desirable to axially stretch the sheath and working channel when positioned on the insertion tube 22 to maintain a tight engagement between an enclosed, transparent end cap of the sheath and the viewing lens 31 of the insertion tube 22, as described more fully, for example, in co-pending, commonly-owned U.S. patent application Ser. No. 09/235,355.

For these reasons, sheaths are commonly constructed of a flexible elastomeric material. A variety of known flexible materials are used for this purpose. Generally speaking, however, such known flexible materials have high coefficients of friction that inhibit the movement of medical instruments through the working channel. In some situations, such as at a sharp bending corner along the insertion tube, the medical instrument may be unable to progress through the working channel, or may even become stuck, necessitating the removal of the insertion tube.

To reduce the coefficient of friction of the internal surface of the working channel, a variety of techniques have been employed. One approach has been to line the working channel with a relatively-hard corrugated material having a low coefficient of friction, such as materials sold under the trademark TEFLON®. Because the relatively-hard corrugated material has a lower coefficient of friction than the flexible material of the working channel, the medical instrument moves more easily through the working channel, and the corrugations allow the necessary bending and axial stretching of the working channel. Unfortunately, the lining of relatively-hard corrugated material greatly increases the thickness of the wall of the working channel, and thus, the overall diameter of the endoscope assembly. Thus, the sheath having a working channel lined with a relatively-hard corrugated material may increase the discomfort or trauma experienced by the patient, or may not be practical for some medical procedures due to size constraints within the patient's body. Also, the cost of manufacturing the working channel lined with the relatively-hard corrugated material is undesirably high. Finally, although the corrugated channel does stretch axially, it does not do so easily.

SUMMARY OF THE INVENTION

The present invention is directed to endoscope assemblies having working channels with reduced bending and stretching resistance. In one embodiment, an endoscope assembly includes a sheath having a body portion adapted to at least partially encapsulate an endoscopic insertion tube, and a working channel attached to the body portion and extending along at least a portion of the body portion. The working channel has a cut disposed therein, the cut being at least partially transverse to a longitudinal axis of the working channel. The working channel is separable along at least a portion of the cut when the working channel is subjected to an axial tension force.

In an alternate embodiment, the working channel has a gap disposed therein, the gap being at least partially transverse to a longitudinal axis of the working channel. The gap is adapted to widen along at least a portion thereof when the working channel is subjected to an axial tension force.

In another embodiment, the working channel is attached to the body portion proximate the distal end and has a sliding portion extending along at least a part of the body portion, the sliding portion being axially slideable along the body portion when the working channel is subjected to an axial force. Alternately, the working channel further includes an expansion section coupled between the sliding portion and the second end, the expansion section including an expansion member that is axially expandable when the working channel is subjected to the axial force.

Endoscope assemblies having a working channel in accordance with the invention advantageously reduce the bending and stretching resistance of the assembly during articulation of the endoscope assembly, thereby reducing the tension on the articulation control cables. Also, because the axial forces (tension and compression) within the working channel are reduced, the working channel can be fabricated out of a relatively hard, inelastic material, thereby reducing the friction within the working channel and improving the physician's ability to perform a medical procedure.

DETAILED DESCRIPTION OF THE INVENTION

The present invention is directed toward endoscopic sheath apparatus and methods, and more specifically, to sheath assemblies having working channels with reduced bending and stretching resistance. Many specific details of certain embodiments of the invention are set forth in the following description and in FIGS. 3–24 to provide a thorough understanding of such embodiments. One skilled in the art, however, will understand that the present invention may have additional embodiments, or that the invention may be practiced without several of the details described in the following description.

Figure 1:
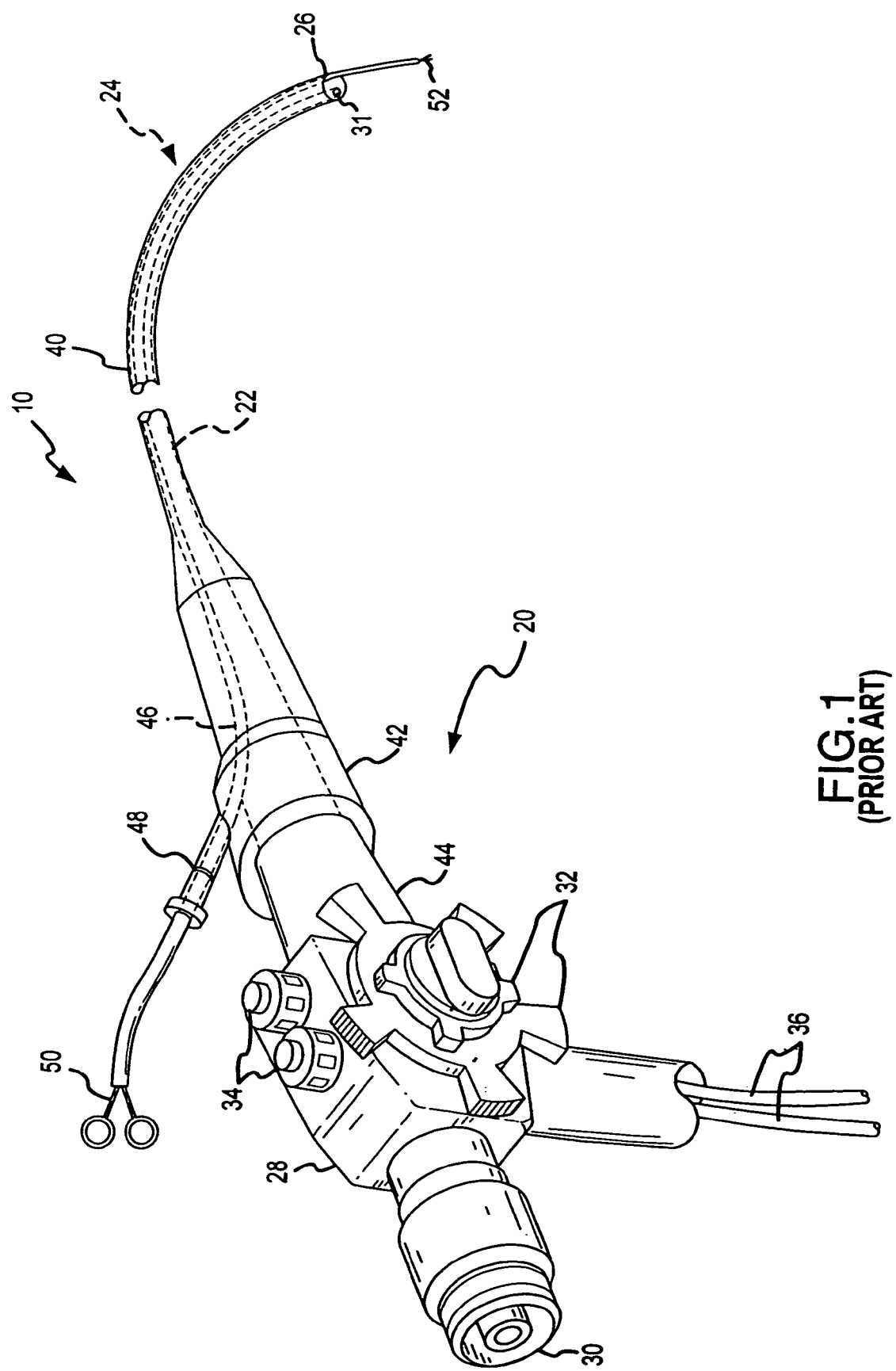
FIG. 1 is an isometric view of an endoscope assembly in accordance with the prior art.
Figure 2:
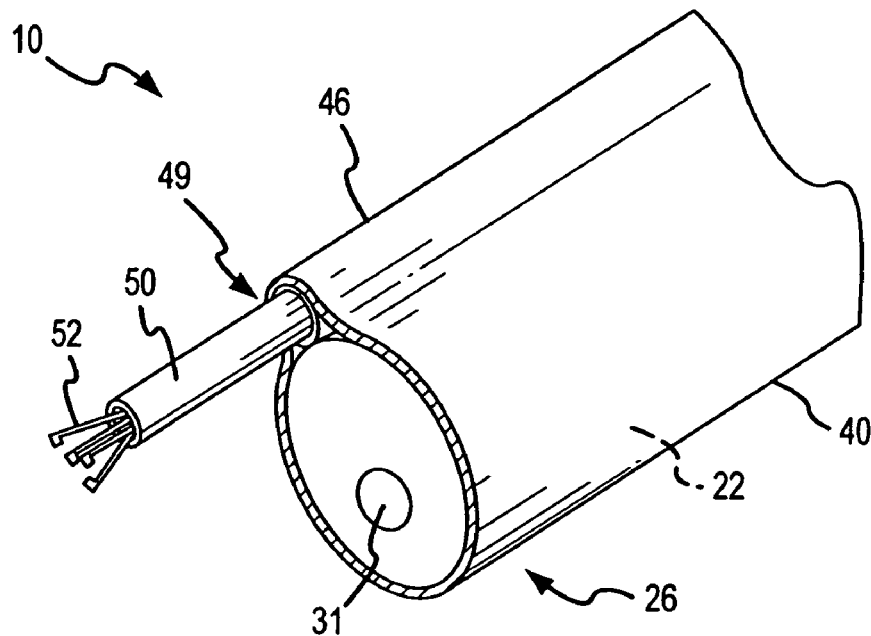
FIG. 2 is a partial isometric view of a distal end of the endoscope assembly of FIG. 1.
Figure 3:
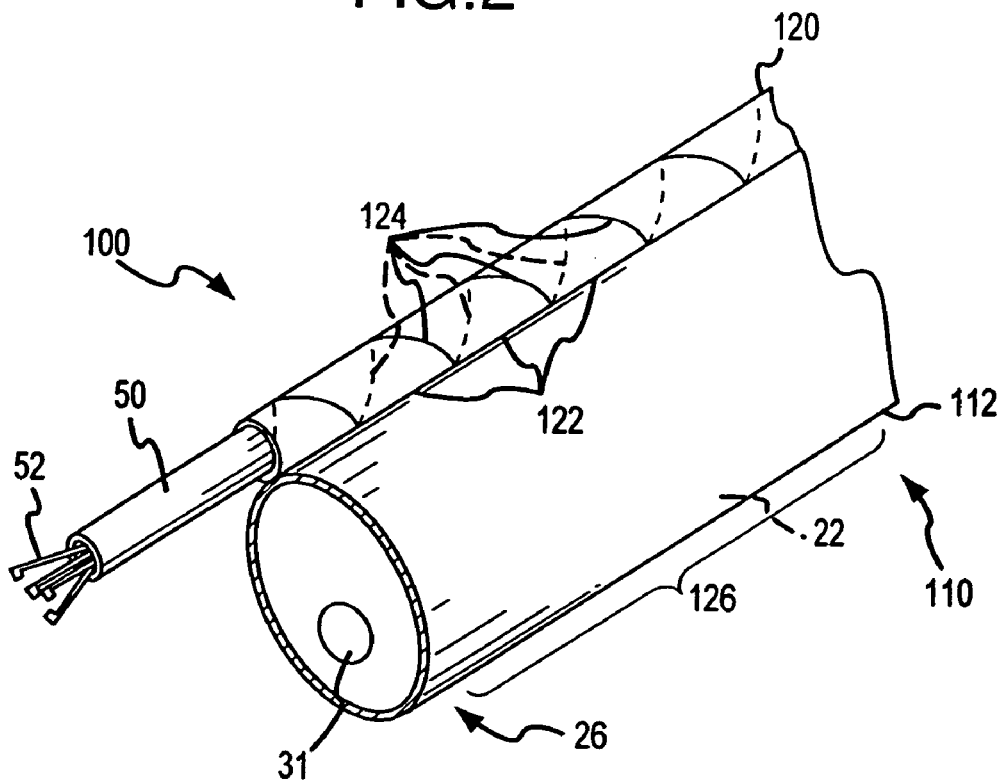
FIG. 3 is a partial isometric view of an endoscope assembly including a sheath in accordance with an embodiment of the invention.

FIG. 3 is a partial isometric view of an endoscope assembly 100 in accordance with an embodiment of the invention. In this embodiment, the endoscope assembly 100 includes a sheath 110 having a tubular body portion 112 that at least partially encapsulates the insertion tube 22 of the endoscope 10 (FIG. 1), and a working channel 120 attached to an outer surface of the tubular body portion 112 at a plurality of attachment points 122. As shown in FIG. 3, the working channel 120 is cut with a spiral (or helical) cut 124 through an outer wall of the working channel 120. The spiral cut 124 may extend along the entire length of the working channel 120, or may extend along only a portion of the working channel 120, such as along a bending section 126 of the insertion tube 22 (FIG. 3).

The working channel 120 may be fabricated from a relatively stiff material having a coefficient of friction that is relatively lower than that of the elastomeric materials commonly used in the prior art, including, for example, materials sold under the trademark TEFLON®, or a variety of relatively hard, relatively inelastic, relatively high durometer polymers, such as urethane, polyvinyl chloride (PVC), acrylic, polycarbonate, polyethylene terephthalate, or other thermoplastic polyesters. Alternately, the working channel 120 may be fabricated from the same elastomeric materials commonly used to fabricate sheaths in the prior art. In a preferred embodiment, the body portion 112 of the sheath 110 is fabricated from an elastomeric material and the working channel 120 is fabricated from a relatively stiff urethane material having a lower coefficient of friction than the elastomeric material of the body portion 112. The urethane working channel 120 may be bonded to the body portion 112 at one or more attachment points 122 using known bonding techniques, such as, for example, an ultraviolet (UV) bonding process or the like.

Figure 4:
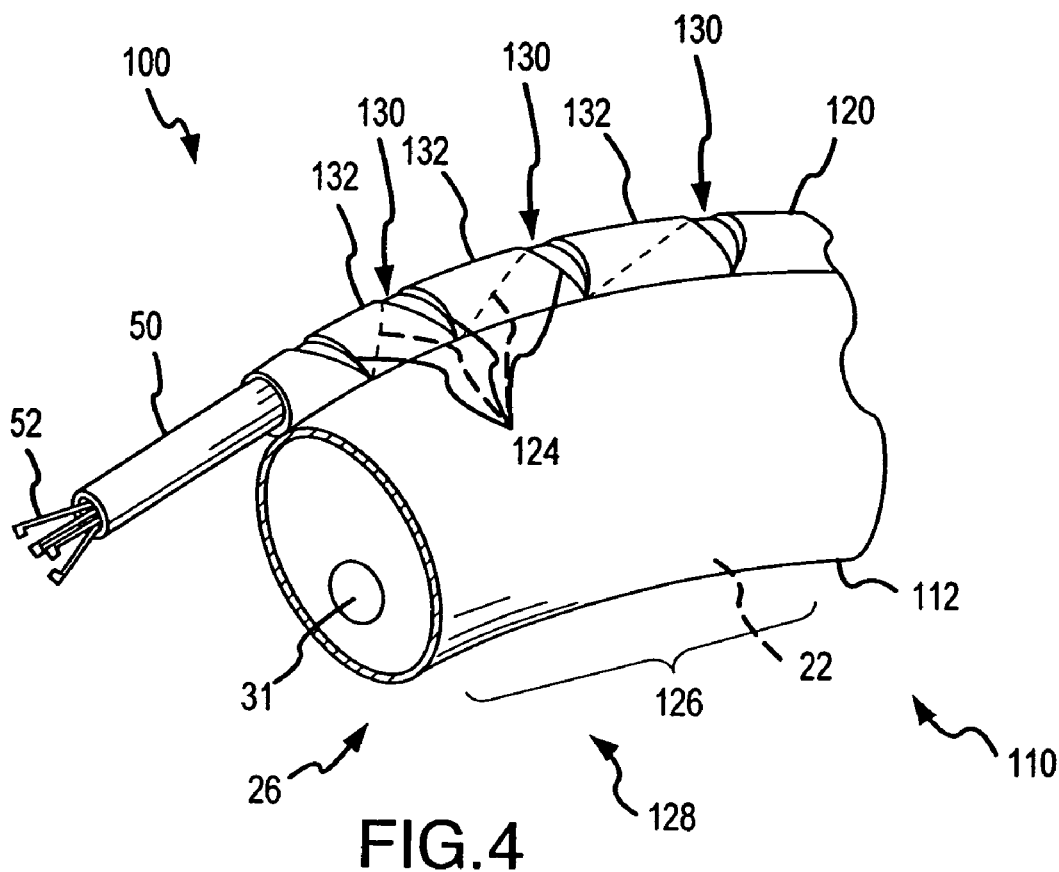
FIG. 4 is a partial isometric view of the endoscope assembly of FIG. 3 in a first articulated position.

FIG. 4 is a partial isometric view of the endoscope assembly 100 of FIG. 3 with the bending section 126 of the insertion tube 22 articulated (or bent) into a first articulated position 128. In the first articulated position 128, the working channel 120 is stretched or extended, causing the spiral cut 124 to separate at one or more locations to form a plurality of gaps 130 between a plurality of channel segments 132. As the bending section 126 of the insertion tube 22 is articulated from a relatively straight position to the first articulated position 128, the widths of the gaps 130 increase, particularly at the outermost portion of each gap (i.e. the portion of each gap 130 that is furthest from the tubular body portion 112 of the sheath 110).

Figure 5:
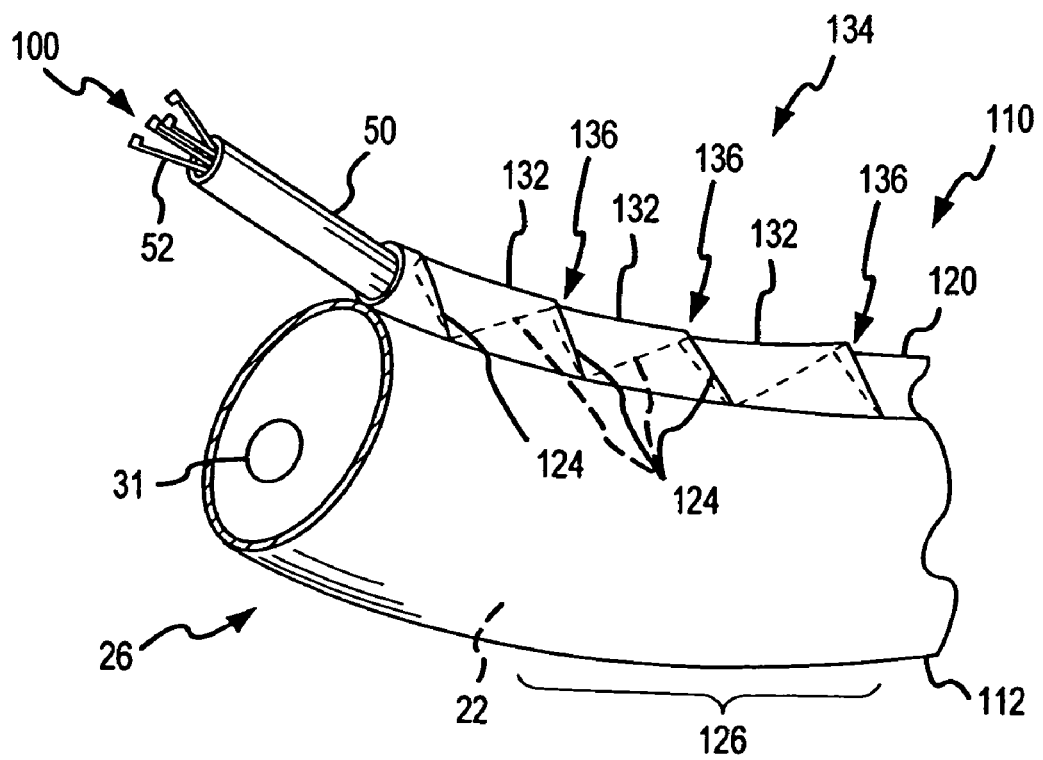
FIG. 5 is a partial isometric view of the endoscope assembly of FIG. 3 in a second articulated position.

FIG. 5 is a partial isometric view of the endoscope assembly 100 of FIG. 3 in a second articulated position 134. In the second articulated position 134, the working channel 120 is compressed. In turn, one or more overlaps 136 are formed between at least some of the plurality of channel segments 132. As the bending section 126 of the insertion tube 22 is articulated from a relatively straight position to the second articulated position 134, the amount of overlap between adjacent channel segments 132 increases, and the number of overlaps 136 formed between channel segments 132 may also increase.

Figure 6:
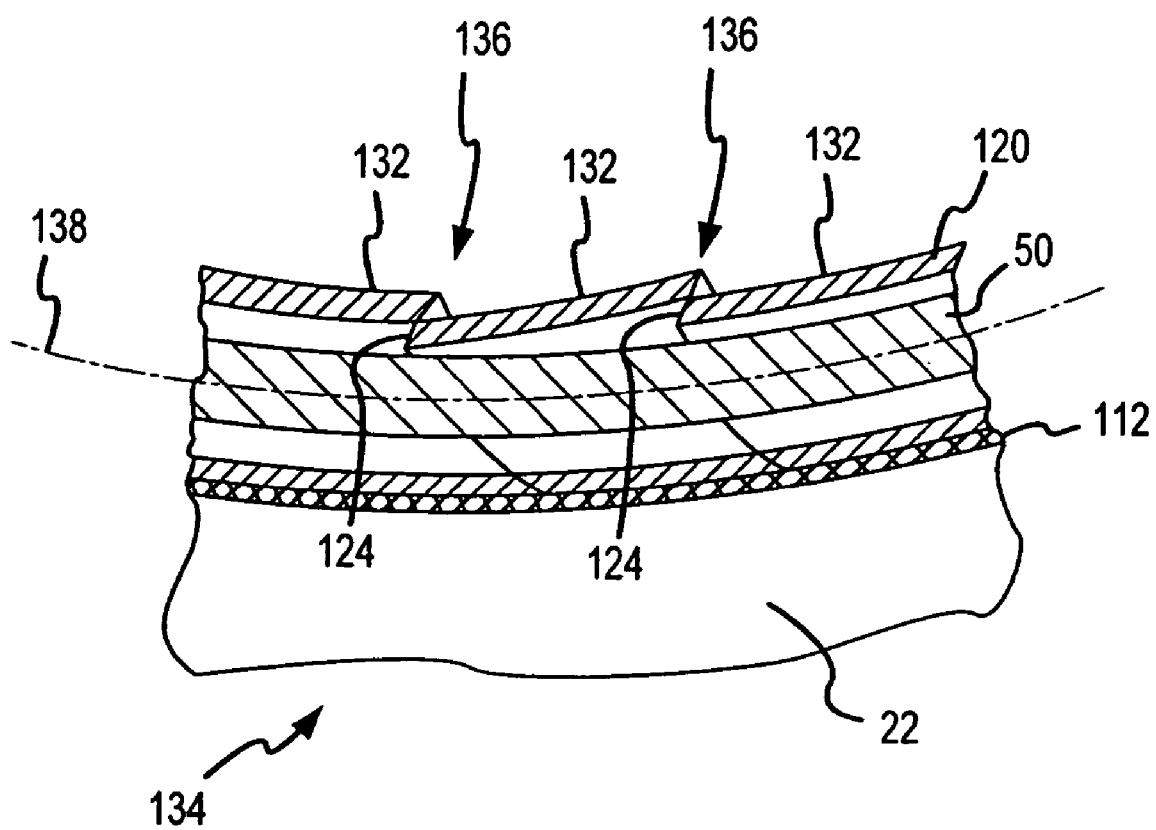
FIG. 6 is an enlarged, partial cross-sectional view of the working channel of FIG. 5.

FIG. 6 is an enlarged, partial cross-sectional view of the endoscope assembly 100 of FIG. 5. As shown in FIG. 6, in the second articulated position 134, the channel segments 132 may become compressed to form overlaps 136. In one embodiment, the spiral cut 124 is not perpendicular to a longitudinal axis 138 of the working channel 120, but rather, is angled (as shown in FIG. 6) so that the ends of the channel segments 132 may more readily slide over each other during compression of the working channel 120.

The working channel 120 having the spiral cut 124 advantageously reduces the bending and stretching resistance of the sheath 110 during articulation of the endoscope assembly 100. As the insertion tube 22 is articulated into the first articulated position 126, the working channel 120 stretches to form the plurality of gaps 130 between the plurality of channel segments 132. The gaps 130 relieve the axial tension forces that would otherwise exist within a stretched prior art working channel, thereby reducing the resistance of the sheath 110 to bending and reducing the amount of force required to articulate and maintain the insertion tube 22 into the first articulated position 126.

Similarly, as the insertion tube 22 is articulated into the second articulated position 134, the working channel 120 is compressed so that the plurality of channel segments 132 move together to form one or more overlaps 136. The overlaps 136 relieve the axial compression forces that would otherwise exist within the prior art working channels, which in turn reduces the resistance of the sheath 110 to bending, and reduces the amount of force required to articulate and maintain the insertion tube 22 into the second articulated position 134.

Furthermore, because the axial forces (tension and compression) within the working channel 120 are reduced by the spiral cut 124, the working channel 120 can be fabricated out of a relatively hard, inelastic material. Thus, the spiral cut 124 advantageously permits the working channel 120 to be fabricated from a relatively hard material having a lower coefficient of friction than the elastomeric materials commonly used in the prior art. Because the friction between the working channel 120 and the medical device 50 is reduced, the physician's ability to perform a medical procedure may be improved.

One may note that several of the specific features of the endoscope assembly 100 may be varied from the embodiment shown in FIGS. 36 and still remain within the scope of the: invention. For example, the pitch or frequency of the spiral cut 124 may be varied to create a greater or fewer number of channel segments 132. Similarly, the angle of the spiral cut 124 may be varied to be more or less oblique to the longitudinal axis 138 of the working channel 120. In alternate embodiments, the spiral cut 124 may extend the entire length of the working channel 120, or may be limited to one or more portions of the working channel 120 as desired, such as, for example, to be adjacent to the portions of greatest bending of the insertion tube 22. The channel 120 can also be installed such that it is in a slightly stretched condition causing gaps to exist when the articulation section is in the neutral position.

Several alternate embodiments of the invention will now be described. In general, the following descriptions of alternate embodiments should not be viewed as an exhaustive list of all possible embodiments contemplated by the inventors to be within the scope of the invention. In the following descriptions, common elements are identified by the same reference numbers as the previously described embodiments. For the sake of brevity, only some of the more significant differences in construction or operation of each embodiment are described in detail.

Figure 7:
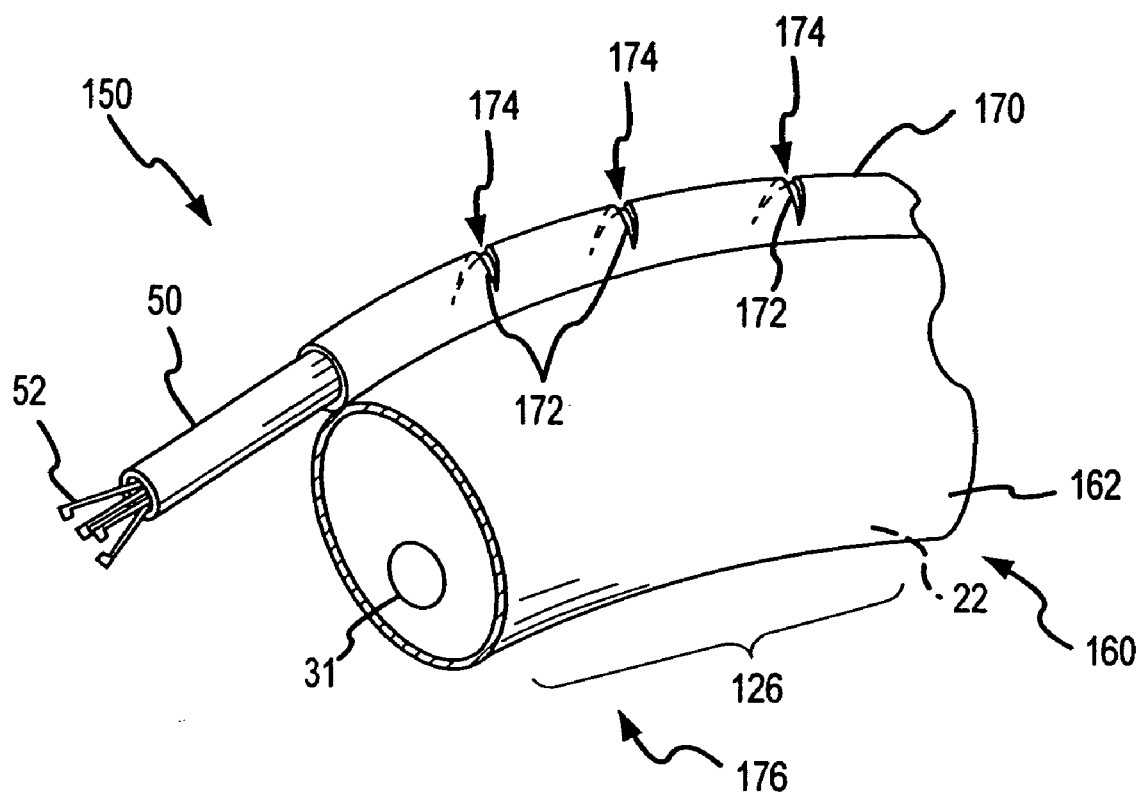
FIG. 7 is a partial isometric view of an endoscope assembly in accordance with an alternate embodiment of the invention.
Figure 8:
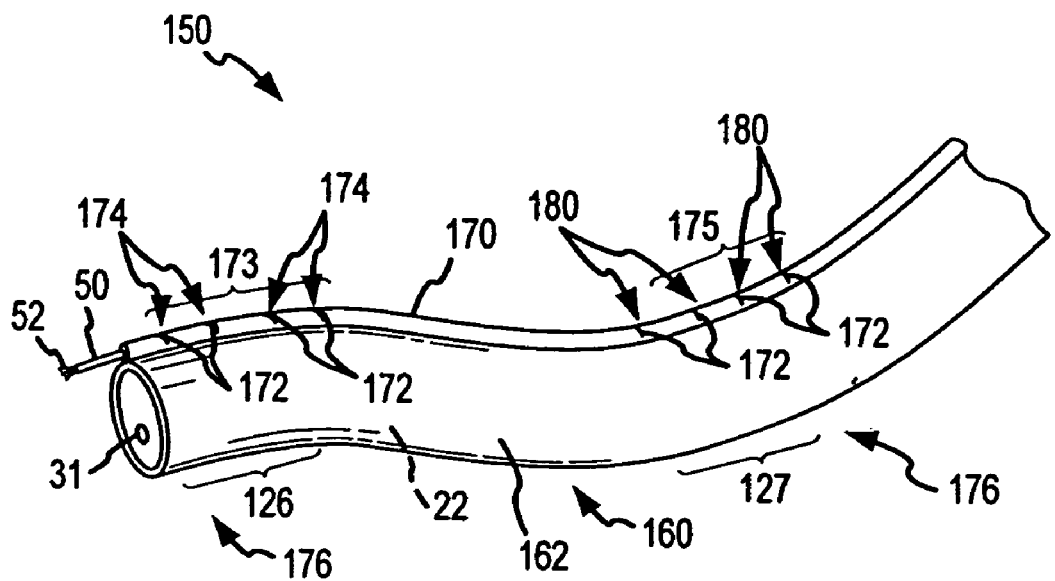
FIG. 8 is another partial isometric view of the endoscope assembly of FIG. 7.

FIG. 7 is a partial isometric view of an endoscope assembly 150 in accordance with an alternate embodiment of the invention. FIG. 8 is another partial isometric view of the endoscope assembly 150 of FIG. 7. In this embodiment, the endoscope assembly 150 includes a sheath 160 having a tubular body portion 162, and a working channel 170 attached thereto. A plurality of partial cuts 172 are disposed through the working channel 170. In the embodiment depicted in FIG. 7, the partial cuts 172 extend approximately half-way through the working channel 170 to form approximately semi-circular cuts. In alternate embodiments, the partial cuts 172 may extend a greater or lesser amount through the working channel 170.

As best shown in FIG. 8, in this embodiment, the working channel 170 has first and second portions 173, 175 having partial cuts 172 disposed therein. The first and second portions 173, 175 are positioned proximate first and second bending portions 126, 127 of the insertion tube 22, respectively.

In operation, when the endoscope assembly 150 is articulated into a first articulated position 176 as shown in FIG. 7, the partial cuts 172 are stretched open to form one or more open notches 174 in the working channel 170. Similarly, when the insertion tube 22 is articulated into a position that compresses the working channel 170 the partial cuts 172 are compressed together to form overlaps 180, in the manner described above and shown in FIGS. 5 and 6.

As described above, the open notches 174 serve to relieve the tension forces within the working channel 170 when the working channel 170 is stretched into the first articulated position 176, and the overlaps 180 relieve the compression forces within the working channel 170 when the working channel 170 is compressed. Therefore, the partial cuts 172 advantageously reduce the resistance of the sheath 110 to bending and articulation of the insertion tube 22, and also reduce the amount of force required to articulate and maintain the insertion tube 22 into an articulated position.

Furthermore, because the axial forces (tension and compression) within the working channel 170 are reduced by the partial cuts 172, the working channel 120 can be fabricated out of a relatively hard, inelastic material. Thus, the partial cuts 172 advantageously permit the working channel 170 to be fabricated from a relatively hard material having a lower coefficient of friction than the elastomeric materials commonly used in the prior art.

Figure 9:
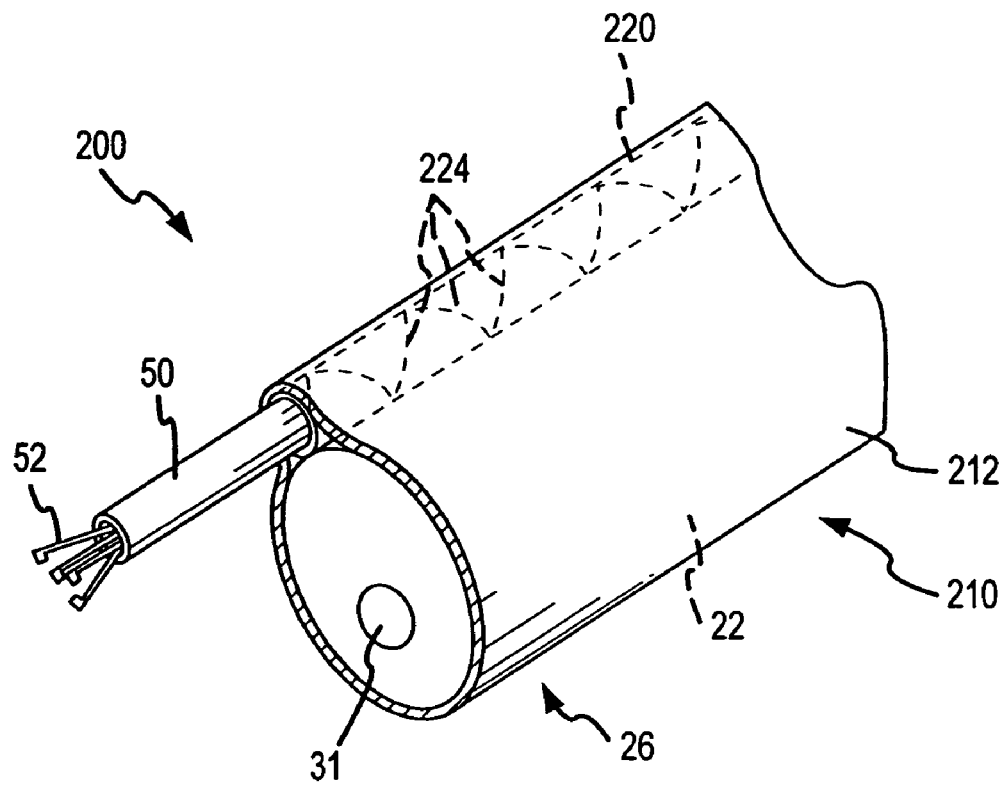
FIG. 9 is a partial isometric view of an -endoscope assembly in accordance with another embodiment of the invention.

FIG. 9 is a partial isometric view of an endoscope assembly 200 in accordance with another embodiment of the invention. The endoscope assembly 200 includes a sheath 210 having a tubular body portion 212 that partially encapsulates the insertion tube 22, and a working channel 220 extending along the insertion tube 22 within the body portion 212 of the sheath 210. The working channel 220 is cut with a spiral cut 224. As described above with respect to the endoscope assembly 100 shown in FIGS. 3–5, when the insertion tube 22 is articulated into positions which stretch or compress the working channel 220, the spiral cut 224 causes the working channel to form gaps 130 or overlaps 136, respectively, thereby relieving the tension or compression stresses that would otherwise form in the working channel 220. In turn, the resistance of the sheath 210 to bending of the insertion tube 22 is reduced.

The sheath 210 of the endoscope assembly 200 advantageously provides the reduced resistance to articulation of the insertion tube 22 as described above, and allows the working channel 220 to be fabricated from a relatively hard material having a lower coefficient of friction than the elastomeric materials commonly used in the prior art. Furthermore, because the working channel 210 is located within the tubular body portion 212, the working channel 210 may be less likely to accumulate foreign matter that may otherwise enter the working channel 210 through the spiral cut 224 during a medical procedure. As a result, the sheath 210 may improve the physician's ability to operate the medical device 50 to perform the desired medical procedure.

Figure 10:
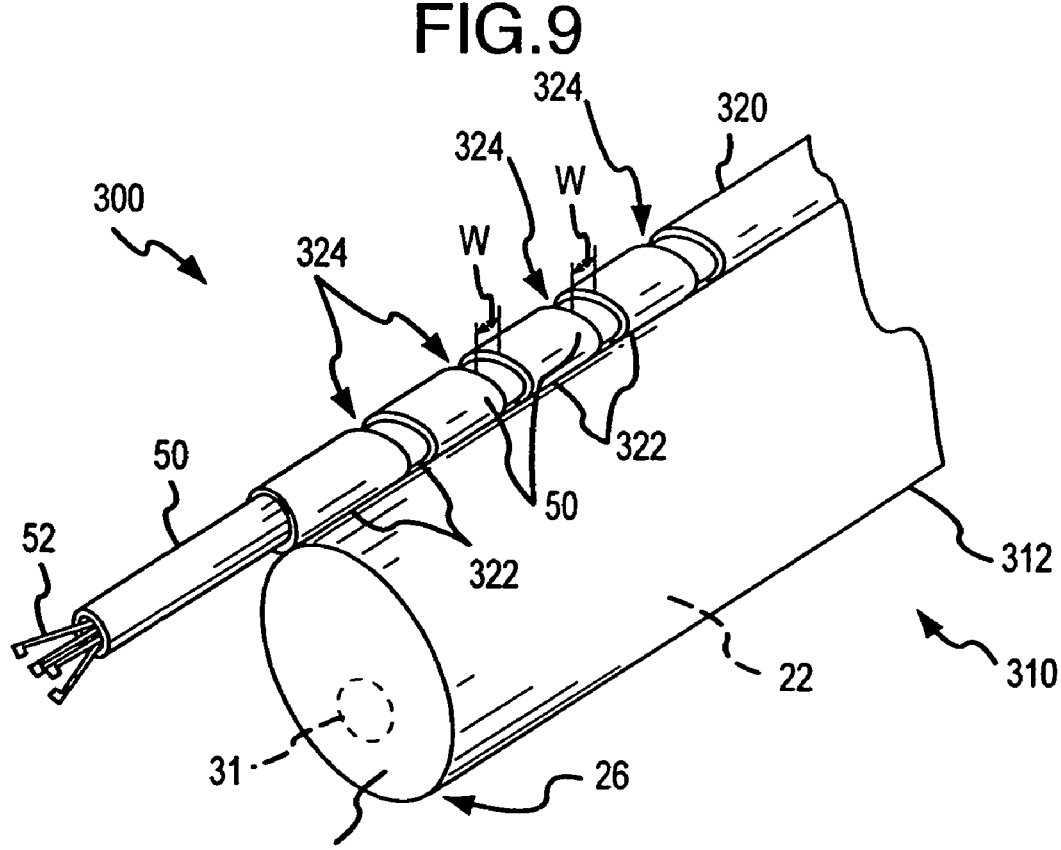
FIG. 10 is a partial isometric view of an endoscope assembly in accordance with another alternate embodiment of the invention.

FIG. 10 is a partial isometric view of an endoscope assembly 300 in accordance with another alternate embodiment of the invention. In this embodiment, the endoscope assembly 300 includes a sheath 310 having a tubular body portion 312 that at least partially encapsulates the insertion tube 22 of the endoscope 10 (FIG. 1), and an end cap 313 that encapsulates the working end 26 of the insertion tube 22. The end cap 313 may be transparent to permit the physician to view a location within the patient's body through the eyepiece 30 and viewing lens 31. A working channel 320 is attached to an outer surface of the tubular body portion 312 at a plurality of attachment points 322. As shown in FIG. 10, a continuous spiral gap 324 is disposed through the outer wall of the working channel 320. The spiral gap 324 has a nominal width w. The spiral gap 324 may extend along the entire length of the working channel 320, or may extend along only a portion of the working channel 320. The medical device 50 is visible through the spiral gap 324.

In one aspect of the above-described embodiment, the nominal width w represents the width of the spiral gap 324 when the sheath 310 is in a relaxed, unstretched position. Alternately, it may be desirable to maintain an axial stretching of the sheath 310 in order to ensure that the end cap 313 is securely engaged against the working end 26 of the insertion tube 22, such as, for example, to permit optimal viewing through the viewing lens 31. In such alternate embodiments, the nominal width w may represent the width of the spiral gap 324 when the sheath 310 is in an axially-stretched position, and therefore, in a relaxed, unstretched position, the spiral gap 324 may have a width that is less than the nominal width w. In one embodiment, the width of the spiral gap 324 when the sheath 310 is in a relaxed, unstretched position is zero, wherein the spiral gap 324 resembles a spiral cut 124 as shown in FIG. 3.

In operation, when the insertion tube 22 is articulated into a position that stretches the working channel 320 (e.g. the first articulated position 128 shown in FIG. 4), the width of the spiral gap 324 may increase over the nominal width w at axial stations proximate to the bending region of the insertion tube 22, thereby reducing the tension forces that would otherwise exist within the working channel 320. Similarly, when the insertion tube 22 is articulated into a position that compresses the working channel 320 (e.g. the second articulated position 134 shown in FIG. 5), the width of the spiral gap 324 may decrease from the nominal width w at axial stations proximate to the bending region.

Figure 11:
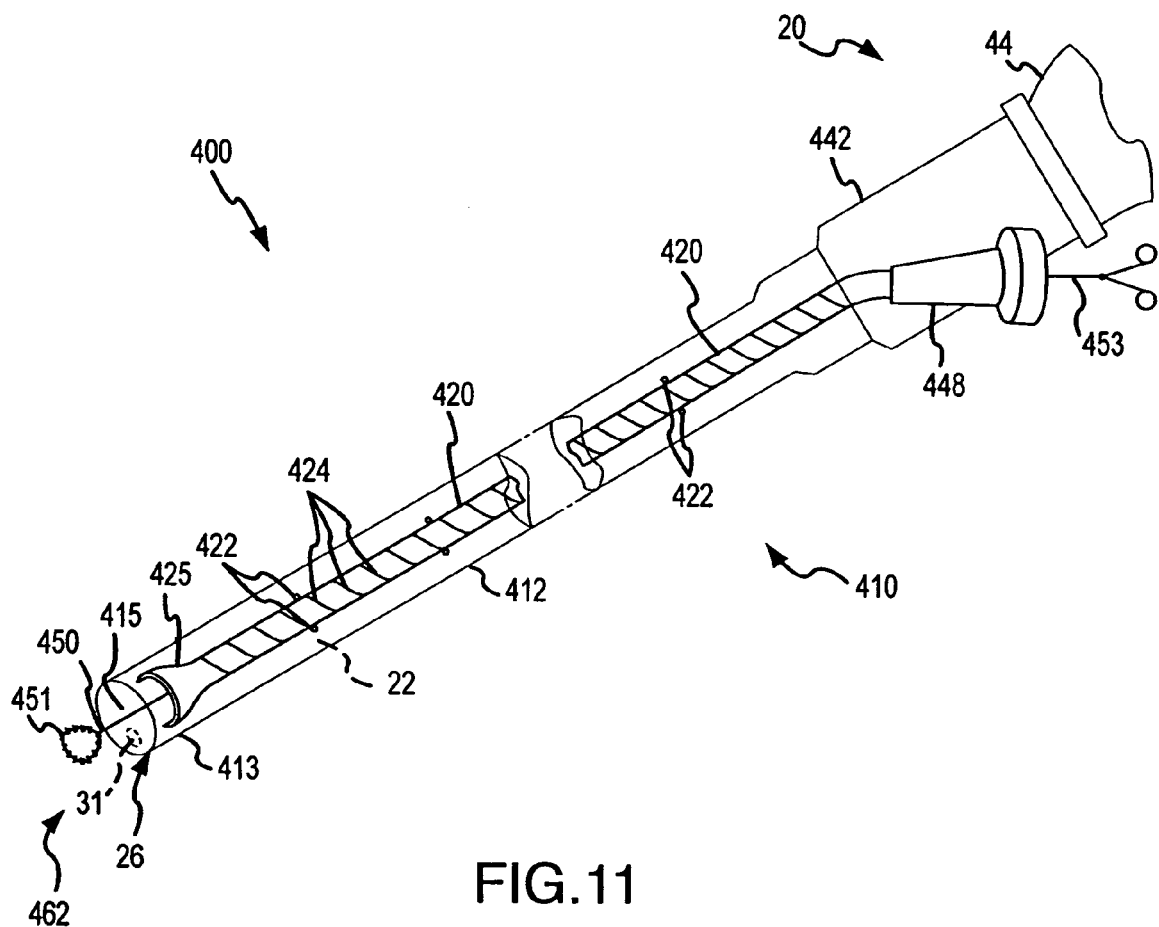
FIG. 11 is a partial isometric view of an endoscope assembly in accordance with yet another embodiment of the invention.
Figure 12:
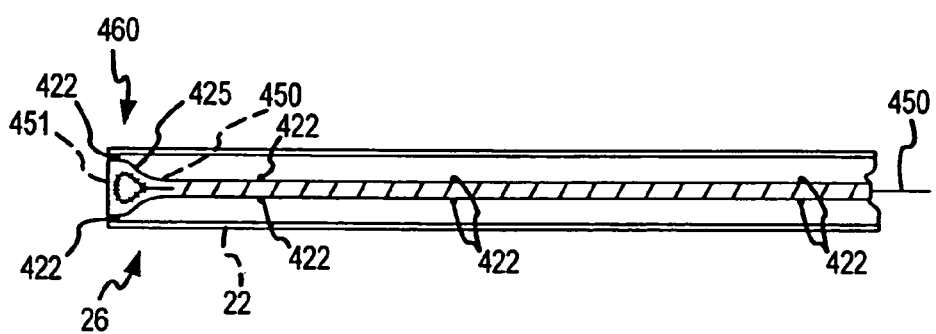
FIG. 12 is a partial elevational view of the endoscope assembly of FIG. 11.

Overall, the sheath 310 having the working channel 320 with the spiral gap 324 disposed therethrough may advantageously reduce the bending and stretching resistance of the sheath 310 during articulation of the endoscope assembly 300. As the insertion tube 22 is articulated, the spiral gap 324 relieves the axial tension and compression forces that would otherwise exist within the working channel, thereby reducing the resistance of the sheath 310 to bending, as well as the amount of force required to articulate and maintain the insertion tube 22 in an articulated position. The spiral gap 324 also allows the working channel 320 to be fabricated from a relatively hard material having a lower coefficient of friction than the elastomeric materials commonly used in the prior art FIG. 11 is a partial isometric view of an endoscope assembly 400 in accordance with yet another embodiment of the invention. FIG. 12 is a partial elevational view of the endoscope assembly 400 of FIG. 11. In this embodiment, the endoscope assembly 400 includes a sheath 410 having a tubular body portion 412, a proximal fitting 442 engageable with the engagement portion 44 of the endoscope 20 (FIG. 1), and an end cap 413 attached to a distal end of the body portion 412. The end cap 413 includes a substantially transparent distal end 415 to enable viewing through the viewing lens 31 of the endoscope 20.

The endoscope assembly 400 further includes a working channel 420 having a spiral cut 424 therethrough, and an enlarged end portion 425 proximate the working end 26 of the insertion tube 22. The enlarged end portion 425 may be sized to receive an operating end 451 of a medical device 450. The working channel 420 further includes an open, proximal end 448 near the endoscope 20. In the embodiment shown in FIG. 11, the proximal end 448 includes an enlarged fitting, such as a well-known Luer lock fitting, to improve the operator's ability to handle the working channel 420 during a medical procedure. A control end 453 of the medical device 450 extends from the proximal end 448 of the working channel 420.

In one embodiment, as shown in FIGS. 11 and 12, the medical device 450 may comprise a biopsy sampling device and the operating end 451 may include a biopsy collection brush of the type described in co-pending, commonly owned U.S. patent application Ser. No. 10/040,923, filed concurrently herewith. A variety of alternate biopsy sampling devices may be used, including, for example, needles, forceps (e.g. U.S. Pat. No. 5,820,630 issued to Lind), loop and cup devices (e.g. U.S. Pat. No. 5,417,697 issued to Wilk et al., U.S. Pat. No. 5,741,271 issued to Nakao et al.), and cylindrical cutting devices (e.g. U.S. Pat. No. 4,651,753 issued to Lifton).

As shown in FIGS. 11 and 12, the working channel 420 is bonded to the body portion 412 of the sheath 410 at a plurality of attachment points 422. In one embodiment, the working channel 420 may be fabricated from a urethane tubing material and the body portion 412 may be fabricated of a commonly used elastomeric material. The enlarged end portion 425 may be fabricated by splitting the urethane tubing along a lengthwise portion thereof, and the urethane tubing may be bonded to the body portion 412 at the attachment points 422 using a well-known UV bonding process. In another aspect, the body portion 412 may be engaged into position onto the insertion tube 22 of the endoscope 20 in an axially-stretched or pre-loaded position. In one preferred embodiment, the body portion 412 is axially stretched between approximately 0.4 inches and approximately 0.6 inches.

In operation, the operating end 451 (e.g. biopsy collection brush) of the medical device 450 may be withdrawn into a retracted or non-operational position 460 as shown in FIG. 12, with the operating end 451 disposed within the enlarged end portion 425 of the working channel 420. The physician may then insert the working end 26 of the endoscope assembly 400 into a patient's body to perform a desired medical procedure. During insertion, as well as during the medical procedure itself, the insertion tube 22 may be articulated into various bending positions using the control knobs 32 (FIG. 1) as described above.

Once the working end 26 is located at the desired position within the patient's body, the medical device 450 may be moved within the working channel 420 to a second or operational position 462, as shown in FIG. 11. In the operational position 462, the operating end 451 is at least partially removed from the enlarged end portion 425 of the working channel 420. The physician may then manipulate the control end 453 of the medical device 450 which extends from the proximal end 448 of the working channel 420 (FIG. 11) to perform the desired medical procedure (e.g. to collect a biopsy sample). After accomplishing the desired procedure, the medical device 450 may be retracted into the first or non-operational position 460 (FIG. 12), and subsequently withdrawn from the patient's body.

The working channel 420 having the spiral cut 424 provides the advantages of reducing the working channel's resistance to bending and articulation of the insertion tube 22, and to axial stretching of the sheath 410, as described above. Furthermore, the enlarged end portion 425 of the working channel 420 may improve the ease of inserting and removing the endoscope assembly 400 from the patient. Because the enlarged end portion 425 at least partially surrounds and covers the operating end 451 in the non-operating position 460, the enlarged end portion 425 may ease the task of inserting (and removing) the endoscope assembly 400 into the patient's body cavity, thereby reducing the trauma to the surrounding tissues and ultimately the discomfort experienced by- the patient. The enlarged end portion 425 may also ensure that the operating end 451 does not become occluded with unwanted or undesirable foreign matter during insertion of the endoscope assembly 400 which might inhibit the physician's ability to perform the desired medical procedure.

Figure 13:
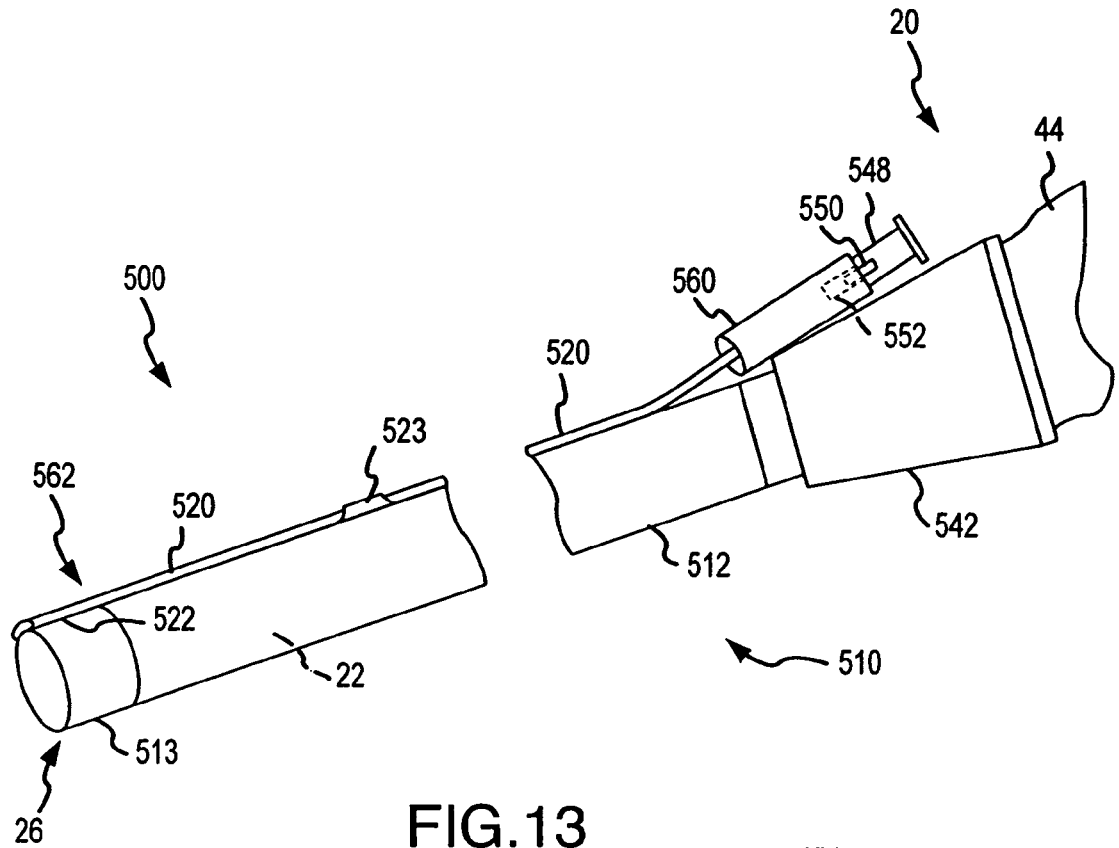
FIG. 13 is a partial isometric view of an endoscope assembly in accordance with a further embodiment of the invention.

FIG. 13 is a partial isometric view of an endoscope assembly 500 in accordance with a further embodiment of the invention. In this embodiment, a sheath 510 having a tubular body 512 is positioned on the insertion tube 22 of the endoscope 20 (FIG. 1), and a collapsible working channel 520 is attached to the body 512 of the sheath 510. The sheath 510 includes an end cap 513 that encloses the working end 26 of the insertion tube 22, and a proximal fitting 548 that fittingly engages the engagement portion 44 of the endoscope 20.

In FIG. 13, the collapsible working channel 520 is shown in a collapsed position 562. In this embodiment, the collapsible working channel 520 is a continuous channel that remains collapsed until a medical device 50 is inserted therethrough. The collapsible working channel 520 may be constructed from collapsible tubing, or any other known collapsible channel structure, including, for example, the collapsible structures disclosed in U.S. Pat. No. 5,025,778 issued to Silverstein et al., incorporated herein by reference. The collapsible working channel 520 is attached to the end cap 513 of the sheath 510 at an attachment point 522. A sleeve support 523 is attached to the body 512 of the sheath 510 along an intermediate portion of the body 512, and the collapsible working channel 520 is slideably engaged within the sleeve support 523.

As further shown if FIG. 13, a fitting 548 is attached to a proximal end of the collapsible working channel 520. In the collapsed position 562, the fitting 548 is partially engaged into a receiver 560 that is attached to the proximal fitting 542 of the sheath 310. The fitting 548 includes at least one tab 550 projecting outwardly therefrom that is slideably engaged in a slot 552 disposed in the receiver 560.

Figure 14:
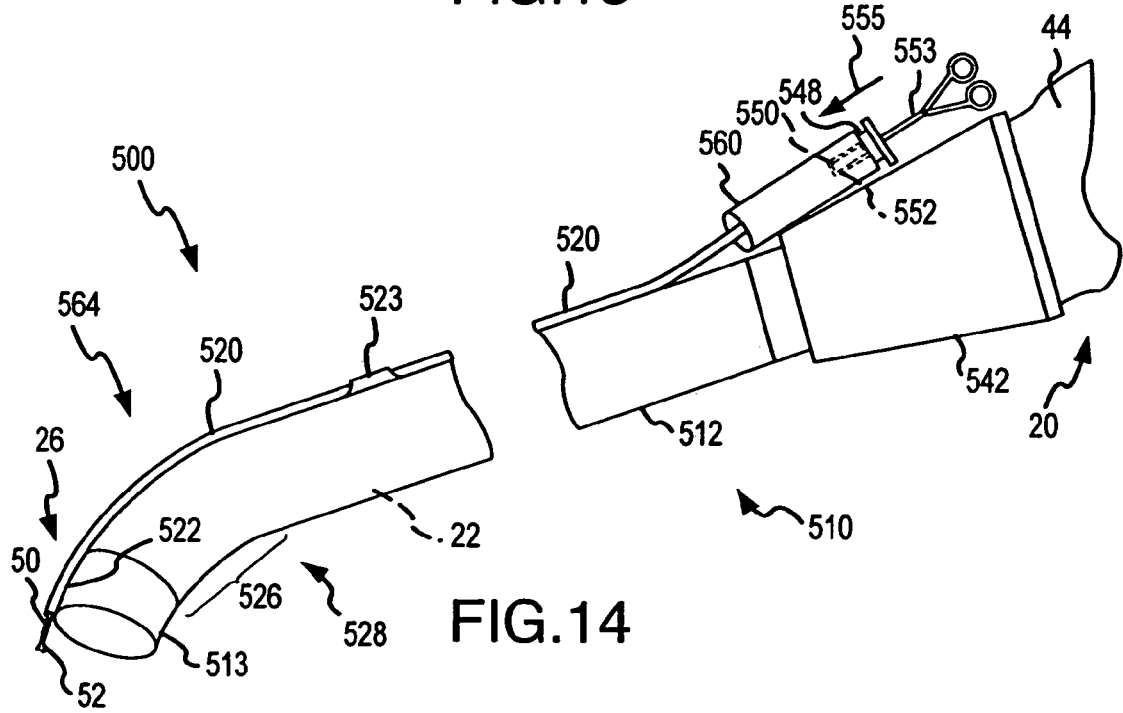
FIG. 14 is a partial isometric view of the endoscope assembly of FIG. 13 in a first articulated position.
Figure 15:
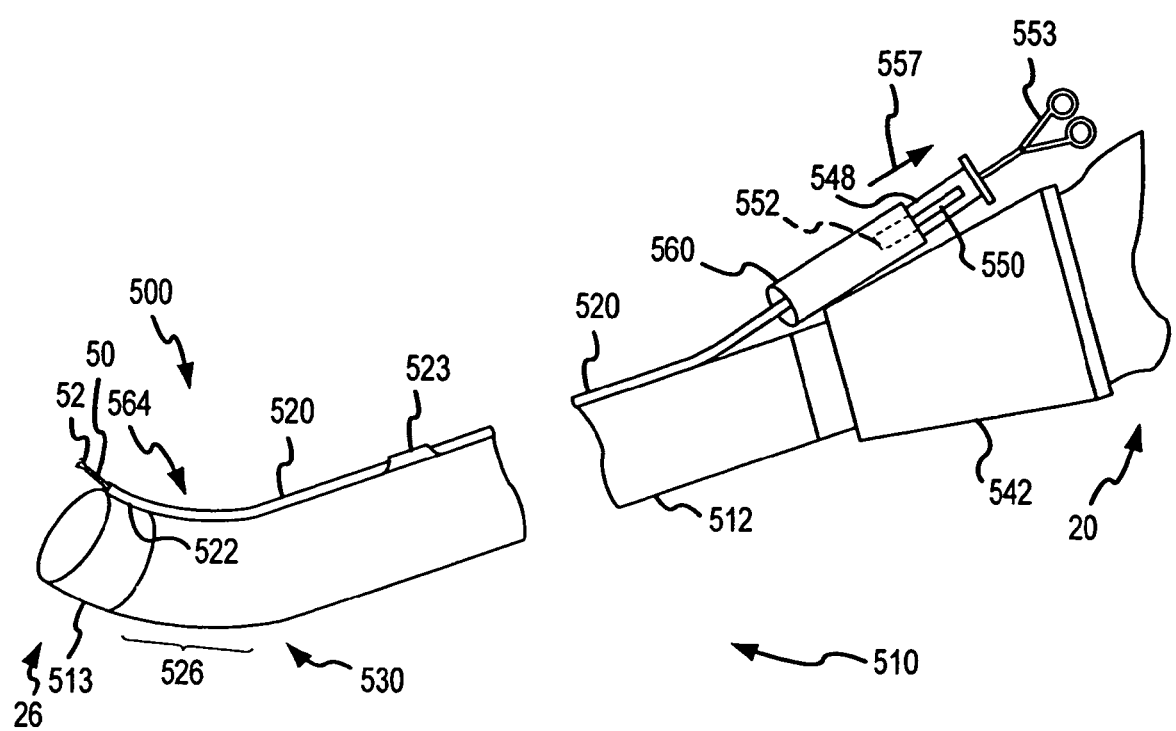
FIG. 15 is a partial isometric view of the endoscope assembly of FIG. 13 in a second articulated position.

FIG. 14 is a partial isometric view of the endoscope assembly 500 in a first articulated position 528 with the collapsible working channel 520 in a non-collapsed position 564. FIG. 15 is a partial isometric view of the endoscope assembly 500 in a second articulated position 530. As shown in FIGS. 14 and 15, a medical device 50 may be inserted through the working channel 520 such that a working portion 52 (e.g. a biopsy sampling device) extends from a distal end of the collapsible working channel 520 and a control end 553 extends from a proximal end of the collapsible working channel 520.

In operation, when a bending portion 526 of the insertion tube 22 is articulated into the first articulated position 528 (FIG. 14), the collapsible working channel 520 is pulled by the insertion tube 22 via the attachment point 522, causing the collapsible working channel 520 to slide through the sleeve support 523, and the fitting 548 to slide in a first direction 555 into the receiver 560. Similarly, when the bending portion 526 is articulated into the second articulated position 530 (FIG. 15), the collapsible working channel 520 is pushed, causing the collapsible working channel 520 to slide through the sleeve support 523, and the fitting 548 to slide in a second direction 557 out of the receiver 560.

One may note that several of the details of the endoscope assembly 500 may be varied from the specific embodiment shown in FIGS. 13–15. For example, the collapsible working channel 520 may be replaced with a regular, non-collapsible working channel (e.g. a flexible tube). Alternately, the collapsible working channel 520 may be replaced in whole or in part with any of the working channel embodiments described above and shown in FIGS. 3–12, except that such alternate embodiments of working channels would only be fixedly attached to the sheath 510 at the attachment point 522 proximate the working end 26. In further embodiments, the attachment point 522 may be located on the body of the sheath rather than on the end cap 513, or multiple attachment points may be used, or the attachment point may be extended to an attachment area extending from the working end 26 to the bending section 526 of the insertion tube 22. In other embodiments, additional sleeve supports 523 may be added to ensure that the working channel 520 remains in proximity to the body 512 of the sheath 510.

The endoscope assembly 500 advantageously provides reduced resistance to articulation of the endoscope 20 over prior art assemblies. Because the collapsible working channel 520 is allowed to slide along the body 512 of the sheath 510, the collapsible working channel 520 may exert little or no resistance to the articulation of the insertion tube 22. Furthermore, the sheath 210 may be axially stretched onto the insertion tube 22 without a corresponding stretching of the collapsible working channel 520.

Another advantage of the endoscope assembly 500 is that the working channel may be fabricated out of a relatively hard material having a relatively lower coefficient of friction compared with commonly used elastic sheath materials. Because the working channel is allowed to slide along the body of the sheath, the working channel is not required to stretch appreciably in the axial direction. Although the working channel may still be somewhat flexible to permit bending during articulation of the insertion tube, because the working channel is not appreciably stretched, the working channel may be fabricated from a relatively hard material having a low coefficient of friction, thereby reducing the friction within the working channel and improving the ability of the operator to articulate the medical device to perform the desired medical procedure.

Yet another advantage of the endoscope assembly 500 is that the proximate end of the collapsible working channel 520 is permitted to move in the first and second directions 555, 557 without the operator's assistance or handling. Because the fitting 548 slideably moves within the receiver 560, the fitting 548 advantageously permits the collapsible working channel 520 to slide along the body 512 of the sheath 510 without the operator's assistance. The operator's hands are thereby freed for other purposes, allowing the operator to concentrate on proper performance of the medical procedure.

Figure 16:
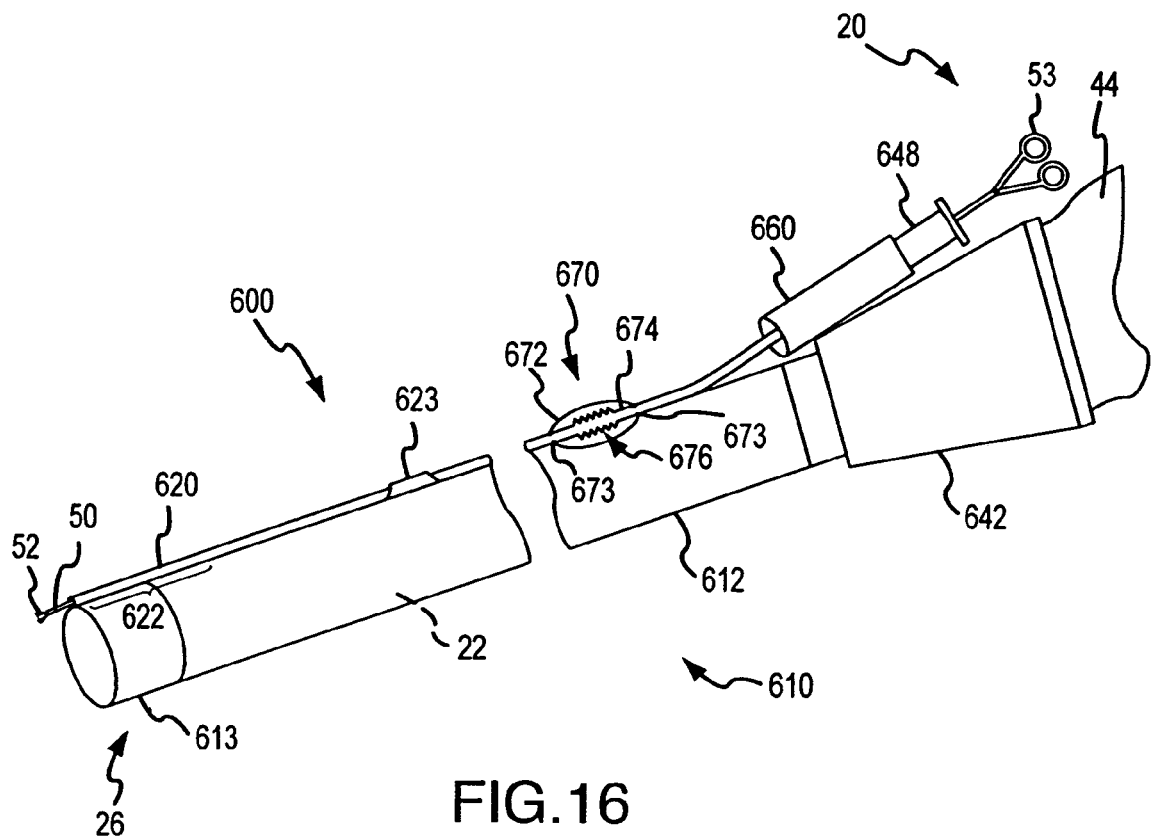
FIG. 16 is a partial isometric view of an endoscope assembly in accordance with another embodiment of the invention.

FIG. 16 is a partial isometric view of an endoscope assembly 600 in accordance with still another embodiment of the invention. In this embodiment, the endoscope assembly 600 includes a working channel 620 having an expansion section 670. For clarity, the expansion section 670 is shown in cut-away, cross-sectional view in FIG. 16 (with a portion of the medical device 50 omitted) so that the internal components of the expansion section 670 are visible. The expansion section 670 includes a flexible outer covering 672 and a corrugated inner member 674. The flexible outer cover 672 is bonded to the adjacent portions of the working channel 620 at bond points 673. The accordian-like inner member 674 has a plurality of corrugations (or pleats) 676 that permit the inner member 674 to be elongated in a lengthwise or axial direction along the length of the working channel 620. In FIG. 16, the corrugated inner member 674 is shown in an unstretched or relaxed position.

The proximal end of the working channel 620 includes a fitting 648 (e.g. a Luer lock fitting) fixedly attached to the proximal fitting 642 of the sheath 610 by a fixed collar 660. In an alternate embodiment, the fixed collar 660 may be eliminated, and the fitting 648 may be directly attached to the sheath 610 or to the endoscope 20. The distal end of the working channel 620 is fixedly attached at an attachment area 622 proximate the working end 26, and is slideably coupled to the body 612 of the sheath 610 by the sleeve support 623. As in the previously described embodiment, the working channel 620 is free to axially slide along the tubular body 612 of the sheath 610 along most of the length of the working channel 620.

Figure 17:
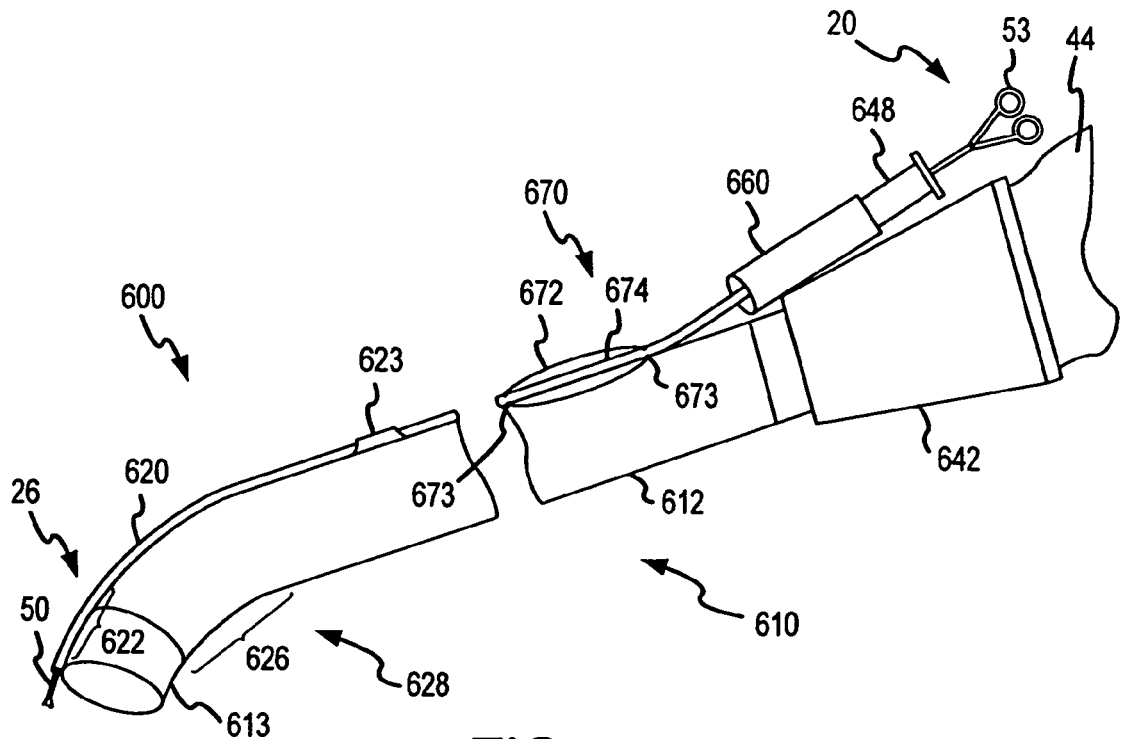
FIG. 17 is a partial isometric view of the endoscope assembly of FIG. 16 in a first articulated position.
Figure 18:
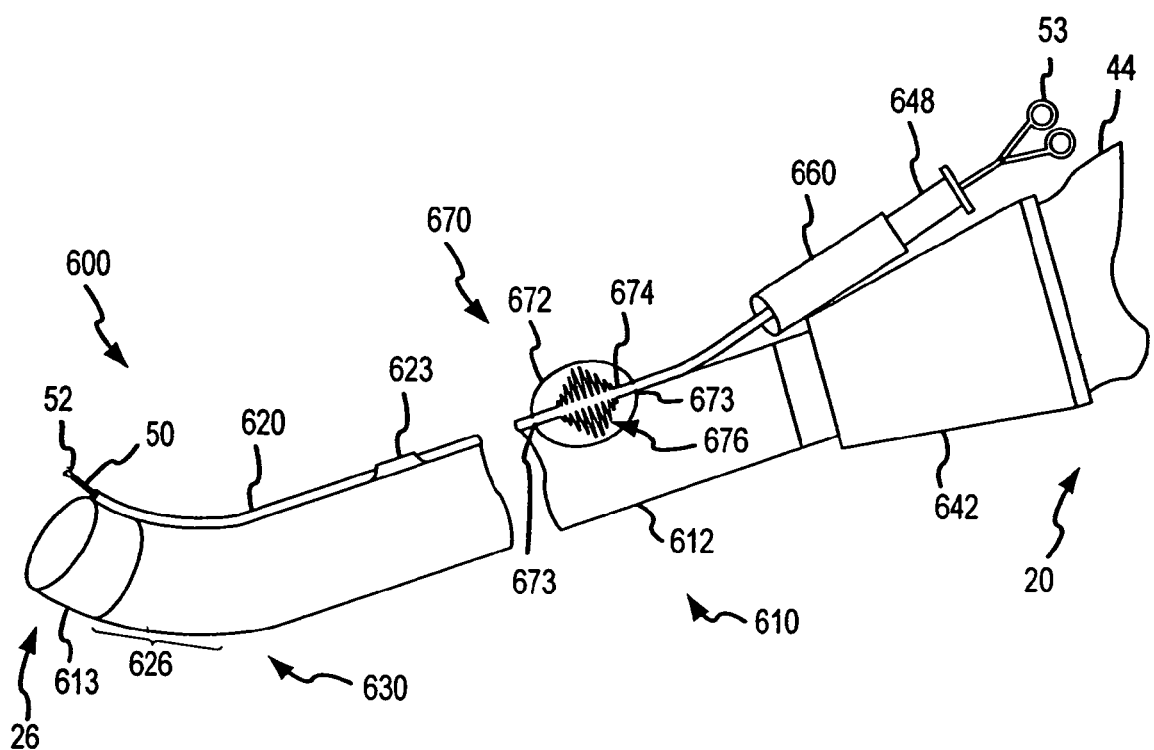
FIG. 18 is a partial isometric view of the endoscope assembly of FIG. 16 in a second articulated position.

FIGS. 17 and 18 show partial isometric views of the endoscope assembly 600 in first and second articulated positions 628, 630, respectively. In operation, as the endoscope assembly 600 is positioned in the first articulated position 628 (FIG. 17), the insertion tube 22 pulls (or tensions) the working channel 620, thereby applying an axial tension force on the expansion section 670. When subjected to the axial tension force, the flexible outer cover 672 stretches and the corrugated inner member 674 elongates in the axial direction. Also, as shown in FIG. 17, the axial tension force causes the corrugations 676 of the inner member 674 expand or flatten, and the bond points 673 becoming spaced farther apart.

As the endoscope assembly 600 is positioned in the second articulated position 630 (FIG. 18), the insertion tube 22 pushes (or compresses) the working channel 620, thereby applying an axial compression force on the expansion section 670. The axial compression force causes the flexible outer cover 672 to slacken, and may even bow outwardly from the corrugated inner member 674. Similarly, the corrugated inner member 674 compresses in the axial direction, with the corrugations 676 become more pronounced and/or greater in number. The inner member 674 may also begin to bow outwardly. As shown in FIG. 18, the axial compression force causes the bond points 673 to become spaced more closely together.

The endoscope assembly 600 advantageously provides reduced resistance to articulation of the endoscope 20 over prior art assemblies. Because the working channel 620 includes the expansion section 670, the working channel 620 may exert little or no resistance to the articulation of the insertion tube 22. Furthermore, the sheath 610 may be axially stretched or pre-loaded onto the insertion tube 22 without a corresponding loading of the working channel 620. The working channel 620 may be beneficial during installation of the assembly 600 when the sheath 610 is being stretched.

Also, because the working channel 620 is not required to stretch appreciably in the axial direction during articulation of the endoscope assembly 600, the working channel may be fabricated out of a relatively hard material having a relatively lower coefficient of friction. Although the working channel may still be flexible enough to permit bending during articulation of the insertion tube, the working channel fabricated from a relatively hard material having a low coefficient of friction may advantageously reduce the friction within the working channel and improve the operator's ability to articulate the medical device to perform the desired medical procedure.

Figure 19:
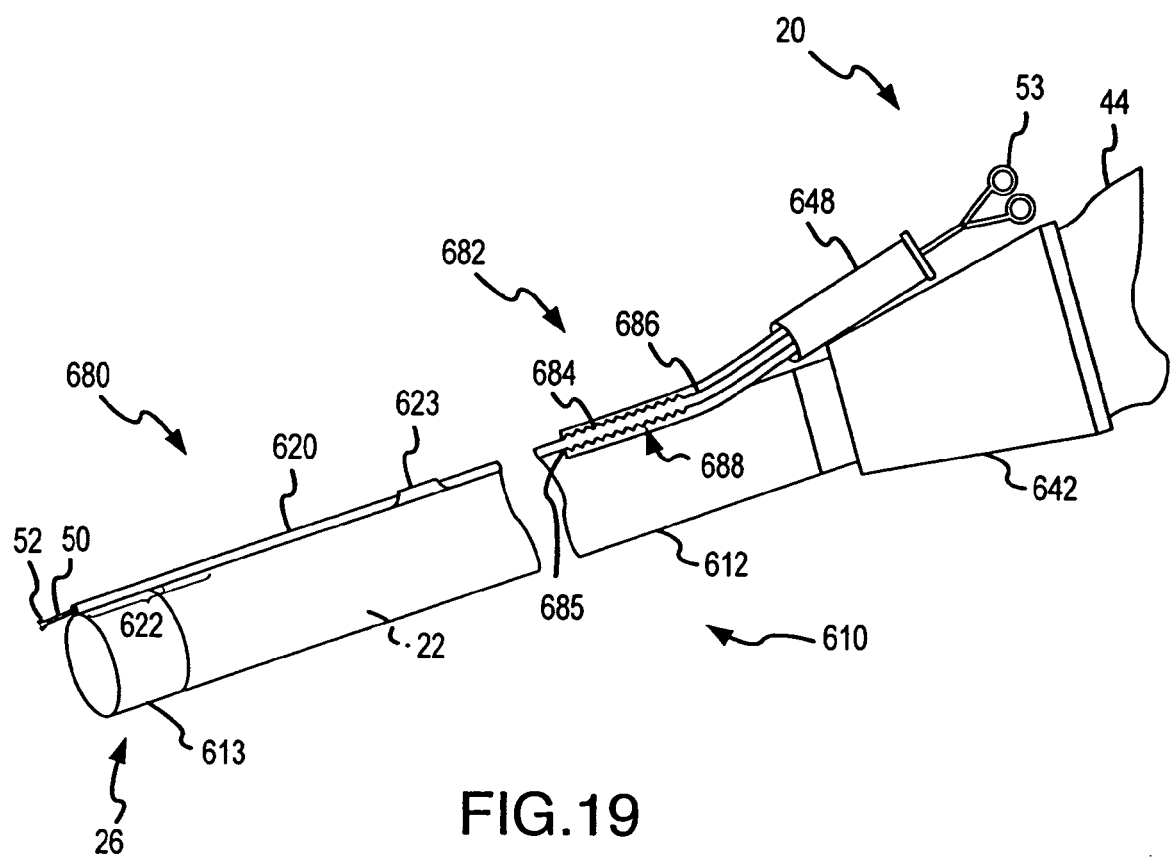
FIG. 19 is a partial isometric view of an endoscope assembly in accordance with another embodiment of the invention.

FIG. 19 is a partial isometric view of an endoscope assembly 680 in accordance with another embodiment of the invention. Similar to the previously-described embodiment, the endoscope assembly 680 shown in FIG. 19 includes a working channel 620 having an expansion section 682, shown in cut-away, cross-sectional view (with a portion of the medical device 50 omitted). The expansion section 682 includes an outer sleeve 684 and a corrugated inner member 686. The inner member 686 is bonded to the adjacent portions of the working channel 620 at bond point 685 and to the fitting 648. The outer sleeve 684 is attached to the fitting 648 but is not bonded to the working channel 620. Again, the accordian-like inner member 686 has a plurality of corrugations (or pleats) 688 that permit the inner member 686 to be elongated in a lengthwise or axial direction along the length of the working channel 620. The fitting 648 is attached to the proximal fitting 642 of the sheath 610. The working channel 620 is flee to axially slide along the tubular body 612 of the sheath 610 along most of the length of the working channel 620. The bond point 685 between the working channel 620 and the inner member 686 is free to axially slide within the outer sleeve 684.

In operation, as the endoscope assembly 682 is positioned in the first articulated position 628 (FIG. 17), the corrugated inner member 686 is elongated in the axial direction, causing the corrugations 688 of the inner member 686 to expand or flatten and drawing the bond point 685 toward the working end 26 of the insertion tube 22. Because the outer sleeve 684 is not attached to the working channel 620, the bond point 685 moves inside the outer sleeve 684 toward the working end 26, and the outer sleeve 684 is not tensioned or stretched during this movement. As the endoscope assembly 680 is positioned in the second articulated position 630 (FIG. 18), the insertion tube 22 pushes (or compresses) the corrugated inner member 686 in the axial direction, with the corrugations 688 becoming more pronounced and/or greater in number. In turn, the bond point 685 moves within the outer sleeve 684 away from the working end 26 of the insertion tube 22. Because the outer sleeve 684 is not attached to the working channel 620, the working channel 620 and the bond point 685 slide within the outer sleeve 684. Consequently, the outer sleeve 684 is not compressed and does not bow outwardly during articulation of the insertion tube 22 into the second articulated position 630.

The endoscope assembly 680 provides the above-noted advantages of reducing the resistance of the working channel 620 to articulation of the endoscope 20, and also allowing the working channel 620 to be fabricated out of a relatively hard material having a relatively lower coefficient of friction. Furthermore, because the outer sleeve 684 of the expansion section 682 maintains a constant diameter and does not bow outwardly during articulation of the insertion tube 22, the expansion section 682 may advantageously be positioned within the patient's body during a medical procedure without causing undue expansion of or trauma to the surrounding tissues during articulation of the insertion tube 22.

Figure 20:
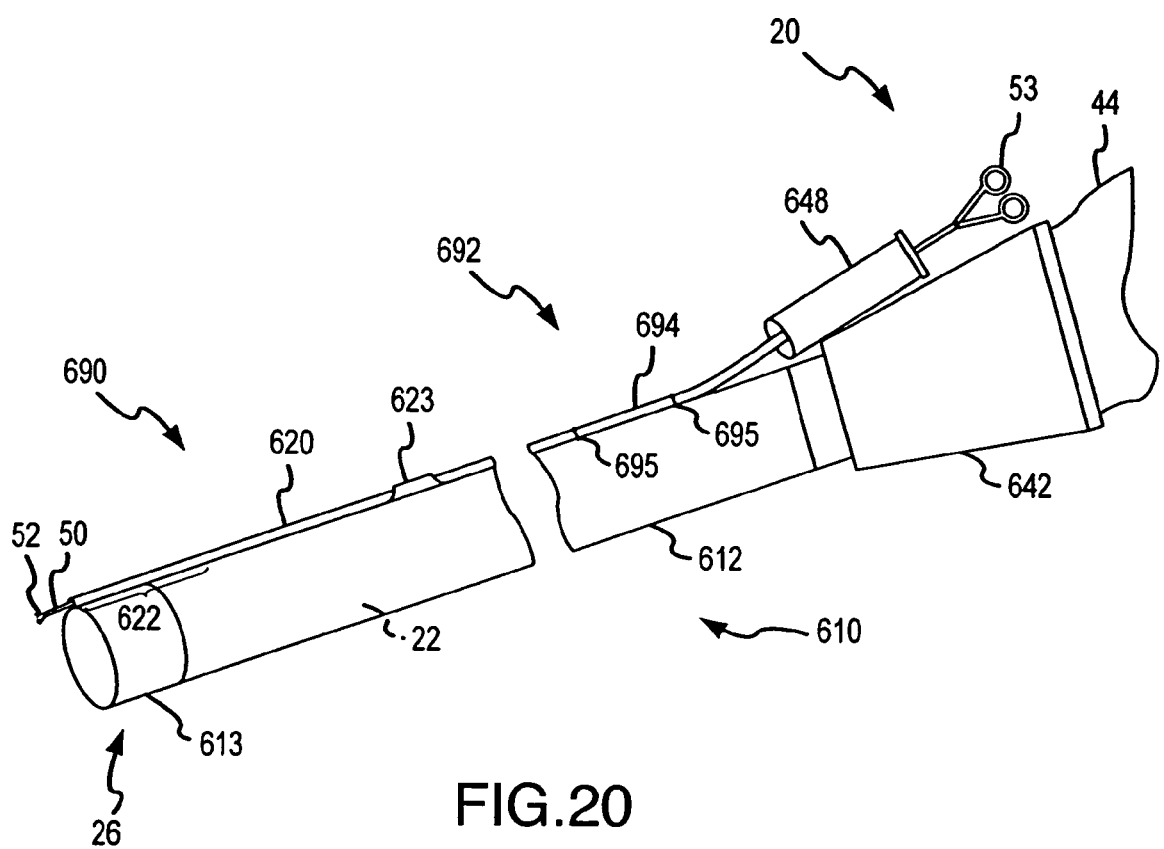
FIG. 20 is a partial isometric view of an endoscope assembly in accordance with still another embodiment of the invention.

FIG. 20 is a partial isometric view of an endoscope assembly in accordance with still another embodiment of the invention. In this embodiment, the endoscope assembly 690 includes an expansion section 692 that includes a flexible resilient portion 694 coupled at bond points 695 between the working channel 620 and the fitting 648. The working channel 620 may be fabricated from a relatively hard material having a relatively lower coefficient of friction. The flexible resilient portion 694 is fabricated from a flexible material, allowing the flexible resilient portion 694 to axially stretch and contract during articulation of the insertion tube 22. Although the flexible resilient portion 694 may be positioned at a variety of axial stations along the insertion tube 22, preferably the flexible resilient portion 694 is positioned adjacent a non-bending portion of the insertion tube 22.

In operation, as the endoscope assembly 690 is positioned in the first articulated position 628 (FIG. 17), the flexible resilient portion 694 is stretched in the axial direction. Conversely, as the endoscope assembly 690 is positioned in the second articulated position 630 (FIG. 18), the flexible resilient portion 694 axially contracts. Preferably, the inner diameter of the flexible resilient portion 694 is sized so that as the flexible resilient portion 694 is stretched, the inner diameter remains large enough for the medical device 50 to continue to move reasonably freely within the flexible resilient portion 694, thereby allowing the physician to conduct the desired medical procedure. In another preferred aspect, the flexible resilient portion 694 may be axially stretched or pre-loaded when the insertion tube 22 is in a relatively straight position, as shown in FIG. 20. By pre-loading the flexible resilient portion 694, when the insertion tube 22 is articulated into the second articulated portion 630 (FIG. 18), the flexible resilient portion 694 does not go slack, but rather, simply becomes less stretched but remains under axial tension. Such pre-loading may reduce the possibility of binding or unwanted friction on the medical device 50 due to an overly-relaxed flexible resilient portion 694.

Again, the endoscope assembly 692 provides the above-noted advantages of reducing the resistance of the working channel 620 to articulation of the endoscope 20, and also allowing the working channel 620 to be fabricated out of a relatively hard material having a relatively lower coefficient of friction. Furthermore, the expansion section 692 having a relatively simple flexible resilient portion 694 may be more easily fabricated than alternate expansion section embodiments, thereby reducing the cost of the assembly 692.

Figure 21:
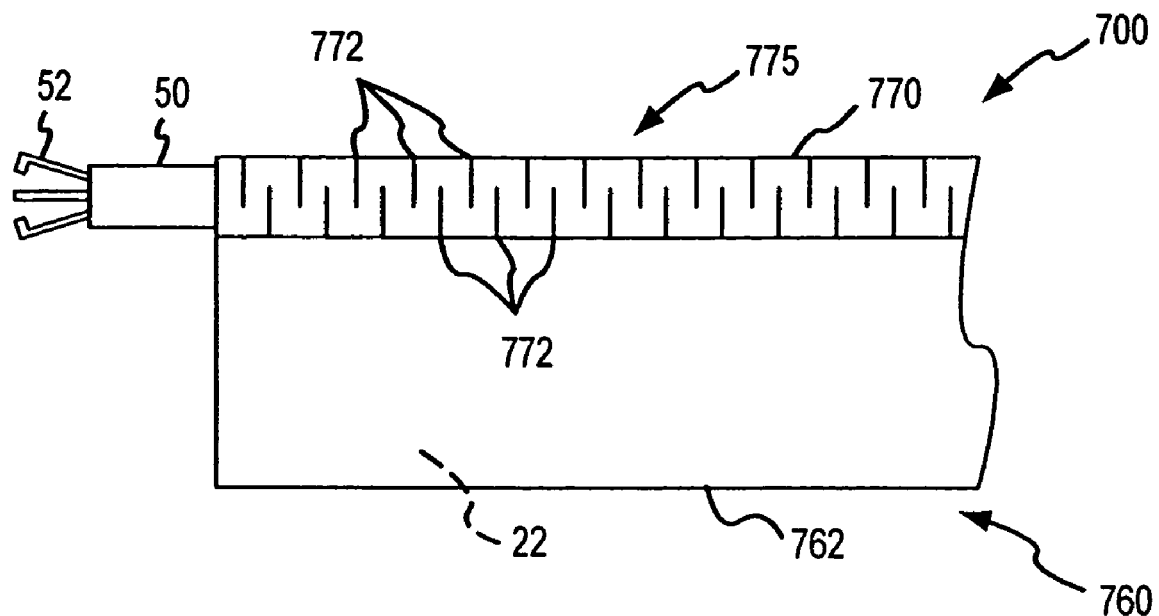
FIG. 21 is a partial elevational view of an endoscope assembly in accordance with a further embodiment of the invention.
Figure 22:
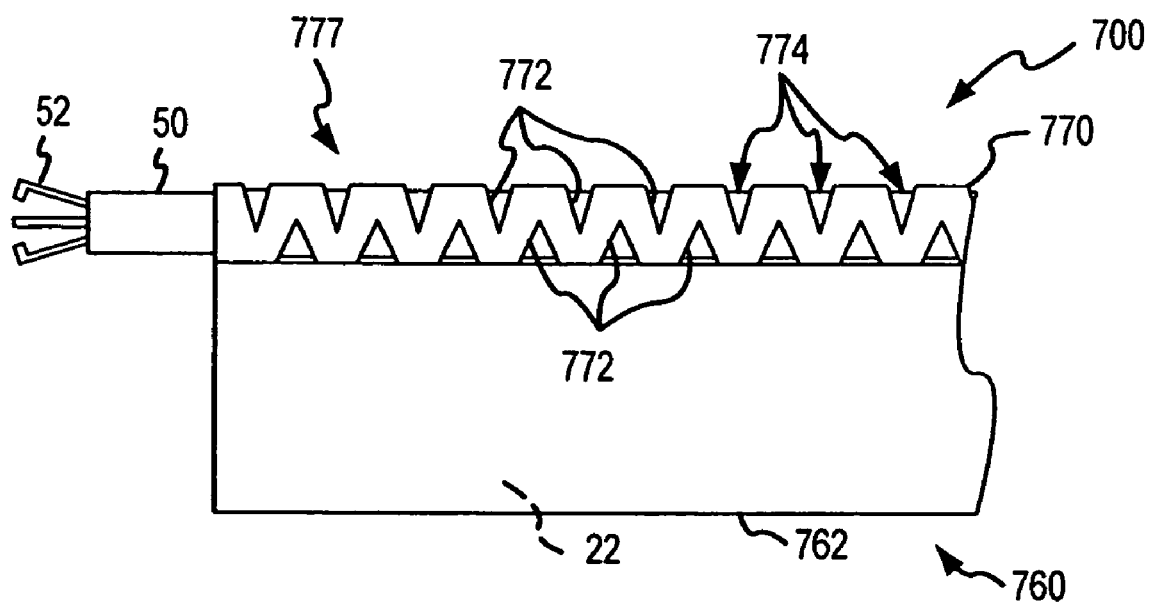
FIG. 22 is another partial elevational view of the endoscope assembly of FIG. 21.

FIGS. 21 and 22 are partial elevational views of an endoscope assembly 700 in accordance with a further embodiment of the invention. In this embodiment, the endoscope assembly 700 includes a sheath 760 having a channel 770 attached to a body portion 762 that at least partially encapsulates the insertion tube 22 of an endoscope 20. A plurality of partial cuts 772 are disposed through the channel 770. In this embodiment, the partial cuts 772 extend into the channel 770 from two sides, that is, from both the inner side (proximate the body portion 762) and the outer side (away from the body portion 762). As best shown in FIG. 21, in this embodiment, the partial cuts 772 are approximately uniformly staggered and extend more than half way through the channel 770. In alternate embodiments, the cuts 772 may be non-uniformly staggered, and may extend a greater or lesser amount through the channel 770 than the embodiment shown in FIGS. 21 and 22.

FIG. 21 shows the endoscope assembly 700 in an unstretched position 775. In this position, the channel 770 is unstretched and the cuts 772 are substantially closed. FIG. 22 shows the channel 770 in a stretched position 777 wherein the cuts 772 are widened to form a plurality of gaps 774. Portions of the medical device 50 are visible through the gaps 774 in FIG. 22.

As described above, the cuts 772 and gaps 774 serve to relieve the axial forces (tension or compression) that would otherwise develop in the channel 770 when the endoscope assembly 700 is articulated during operation, or when the sheath 760 is installed onto the insertion tube 22 in a pre-loaded or stretched position. Thus, the cuts 772 and gaps 774 advantageously reduce the resistance of the endoscope assembly 700 to bending and articulation, and also reduce the amount of force required to maintain the endoscope assembly 700 in an articulated position.

Figure 23:
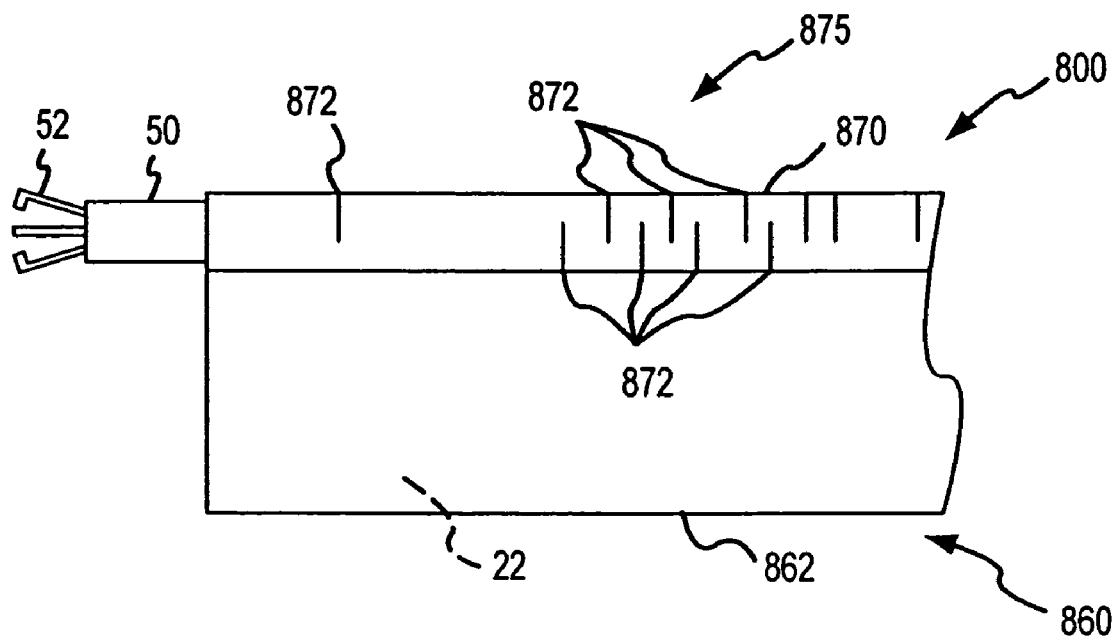
FIG. 23 is a partial elevational view of an endoscope assembly in accordance with yet another embodiment of the invention.
Figure 24:
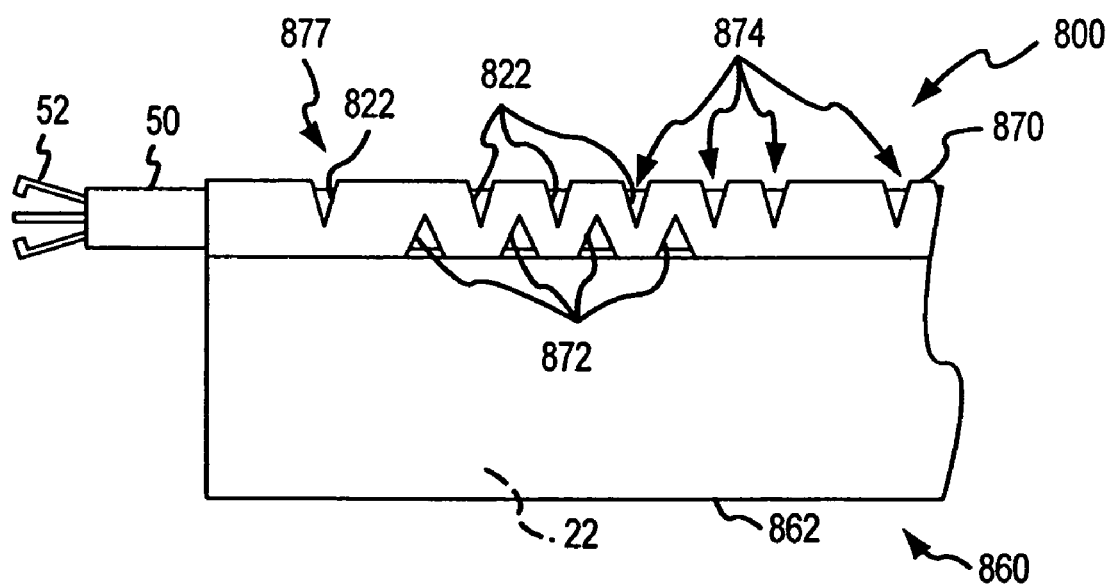
FIG. 24 is another partial elevational view of the endoscope assembly: of FIG. 23.

FIGS. 23 and 24 are partial elevational views of an endoscope assembly 800 in accordance with yet another embodiment of the invention. The endoscope assembly 800 is similar to the previously described embodiment, except that the cuts 872 in the channel 870 are non-uniformly distributed. Again, in this embodiment, the endoscope assembly 800 includes a sheath 860 having a channel 870 attached to a body portion 862 that at least partially encapsulates the insertion tube 22 of an endoscope 20. The cuts 872 extend into the channel 870 from two sides.

FIG. 23 shows the endoscope assembly 800 in an unstretched position 875, in which the channel 870 is unstretched and the cuts 872 are substantially closed. On the other hand, FIG. 24 shows the channel 870 in a stretched position 877 wherein the cuts 872 are widened to form a plurality of gaps 874. Again, portions of the medical device 50 are visible through the gaps 874 in FIG. 24.

The cuts 872 and gaps 874 advantageously serve to relieve the axial forces that would otherwise develop in the channel 870 when the endoscope assembly 800 is articulated during operation, or when the sheath 860 is installed onto the insertion tube 22 in a pre-loaded or stretched position. Thus, the endoscope assembly 800 exhibits reduced resistance to bending and articulation.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other apparatus and methods for endoscope assemblies having working channels with reduced bending and stretching resistance, and not just to the embodiments described above and shown in the accompanying figures. Accordingly, the scope of the invention should be determined from the following claims.

The invention claimed is:

1. A sheath assembly adapted for use with an endoscopic insertion tube, the sheath assembly comprising:
   a body portion adapted to at least partially encapsulate the insertion tube; and
   a working channel attached to the body portion and extending along at least a portion of the body portion, the working channel having a cut disposed therein, the cut being at least partially transverse to a longitudinal axis of the working channel, the working channel being separable along at least a portion of the cut when the working channel is subjected to an axial tension force.

2. The assembly of claim 1 wherein the cut comprises a spiral cut.

3. The assembly of claim 1 wherein the working channel further has a plurality of additional cuts disposed therein, the plurality of additional cuts being at least partially transverse to the longitudinal axis, the working channel being separable along at least a portion of at least some of the plurality of additional cuts when the working channel is subjected to the axial tension force.

4. The assembly of claim 1 wherein the working channel includes a first plurality of additional cuts disposed in a first side thereof and a second plurality of additional cuts disposed in a second side thereof, the additional cuts being at least partially transverse to the longitudinal axis, the working channel being separable along at least a portion of at least some of the additional cuts when the working channel is subjected to the axial tension force.

5. The assembly of claim 4 wherein the second side is substantially opposite from the first side.

6. The assembly of claim 4 wherein the additional cuts are uniformly disposed within the working channel.

7. The assembly of claim 4 wherein the additional cuts are non- uniformly distributed within the working channel.

8. The assembly of claim 1 wherein the cut extends approximately perpendicularly to the longitudinal axis of the working channel.

9. The assembly of claim 1 wherein the cut extends only partially through the working channel.

10. The assembly of claim 1 wherein the cut extends along a portion of the working channel adapted to be approximately aligned with a bending section of the insertion tube.

11. The assembly of claim 1 wherein the working channel is attached to an outer surface of the body portion.

12. The assembly of claim 1 wherein the working channel extends along an inner surface of the body portion and is adapted to be positioned between the body portion and the insertion tube when the body portion is positioned to at least partially encapsulate the insertion tube.

13. The assembly of claim 1 wherein the working channel is adapted to overlap along at least a second portion of the, cut when the working channel is subjected to an axial compression force.

14. The assembly of claim 1 wherein the working channel is attached to the body portion at a plurality of attachment points.

15. The assembly of claim 1 wherein the working channel is adapted to slideably receive at least a portion of a medical device having an operating end, the working channel comprising an enlarged end portion proximate an end of the body portion, the enlarged end portion being adapted to at least partially receive the operating end of the medical device.

16. The assembly of claim 1 wherein the working channel comprises a channel fabricated from a material selected from the group consisting of TEFLON®, urethane, polyvinyl chloride (PVC), acrylic, polycarbonate, and polyethylene terephthalate.

17. The assembly of claim 1 wherein the body portion includes an end cap adapted to encapsulate a working end of the insertion tube.

18. An endoscopic assembly, comprising:
   an elongated insertion tube;
   a sheath assembly including a body portion at least partially encapsulating the insertion tube; and
   a working channel attached to the body portion and extending along at least a portion of the body portion, the working channel having a cut disposed therein, the cut being at least partially transverse to a longitudinal axis of the working channel, the working channel being separable along at least a portion of the cut when the working channel is subjected to an axial tension force.

19. The assembly of claim 18 wherein the cut comprises a spiral cut.

20. The assembly of claim 18 wherein the working channel further has a plurality of additional cuts disposed therein, the plurality of additional cuts being at least partially transverse to the longitudinal axis, the working channel being separable along at least a portion of at least some of the plurality of additional cuts when the working channel is subjected to the axial tension force.

21. The assembly of claim 18 wherein the working channel includes a first plurality of additional cuts disposed in a first side thereof and a second plurality of additional cuts disposed in a second side thereof, the additional cuts being at least partially transverse to the longitudinal axis, the working channel being separable along at least a portion of at least some of the additional cuts when the working channel is subjected to the axial tension force.

22. The assembly of claim 21 wherein the second side is substantially opposite from the first side.

23. The assembly of claim 21 wherein the additional cuts are uniformly disposed within the working channel.

24. The assembly of claim 21 wherein the additional cuts are non- uniformly distributed within the working channel.

25. The assembly of claim 18 wherein the cut extends approximately perpendicularly to the longitudinal axis of the working channel.

26. The assembly of claim 18 wherein the cut extends only partially through the working channel.

27. The assembly of claim 18 wherein the insertion tube includes a bending section, and wherein the cut extends along a portion of the working channel approximately aligned with the bending section of the insertion tube.

28. The assembly of claim 18 wherein the working channel is attached to an outer surface of the body portion.

29. The assembly of claim 18 wherein the working channel extends along an inner surface of the body portion and is positioned between the body portion and the insertion tube.

30. The assembly of claim 18 wherein the working channel overlaps along at least a second portion of the cut when the working channel is subjected to an axial compression force.

31. The assembly of claim 18 wherein the working channel is attached to the body portion at a plurality of attachment points.

32. The assembly of claim 18 wherein the working channel is adapted to slideably receive at least a portion of a medical device having an operating end, the working channel comprising an enlarged end portion proximate an end of the body portion, the enlarged end portion being adapted to at least partially receive the operating end of the medical device.

33. The assembly of claim 18, further comprising a headpiece attached to the insertion tube.

34. The assembly of claim 18 wherein the working channel comprises a channel fabricated from a material selected from the group consisting of TEFLON®, urethane, polyvinyl chloride (PVC), acrylic, polycarbonate, and polyethylene terephthalate.

35. The assembly of claim 18 wherein the body portion includes an end cap that encapsulates a working end of the insertion tube.

36. A sheath assembly adapted for use with an endoscopic insertion tube, the sheath assembly comprising:

a body portion adapted to at least partially encapsulate the insertion tube; and a working channel attached to the body portion and extending along at least a portion of the body portion, the working channel having a gap disposed therein, the gap being at least partially transverse to a longitudinal axis of the working channel, the gap being adapted to widen along at least a portion thereof when the working channel is subjected to an axial tension force.

37. The assembly of claim 36 wherein the gap comprises a spiral gap.

38. The assembly of claim 36 wherein the working channel further has a plurality of additional gaps disposed therein, the plurality of additional gaps being at least partially transverse to the longitudinal axis, the working channel being adapted to widen along at least a portion of at least some of the additional gaps when the working channel is subjected to the axial tension force.

39. The assembly of claim 36 wherein the working channel includes a first plurality of additional gaps disposed in a first side thereof and a second plurality of additional gaps disposed in a second side thereof, the additional gaps being at least partially transverse to the longitudinal axis, the working channel being adapted to widen along at least a portion of at least some of the additional gaps when the working channel is subjected to the axial tension force.

40. The assembly of claim 39 wherein the second side is substantially opposite from the first side.

41. The assembly of claim 39 wherein the additional gaps are uniformly disposed within the working channel.

42. The assembly of claim 39 wherein the additional gaps are non- uniformly disposed within the working channel.

43. The assembly of claim 36 wherein the gap extends along a portion of the working channel adapted to be approximately aligned with a bending section of the insertion tube.

44. The assembly of claim 36 wherein the working channel is attached to an outer surface of the body portion.

45. The assembly of claim 36 wherein the working channel extends along an inner surface of the body portion and is adapted to be positioned between the body portion and the insertion tube when the body portion is positioned to at least partially encapsulate the insertion tube.

46. The assembly of claim 36 wherein the gap being adapted to narrow along at least a portion thereof when the working channel is subjected to an axial compression force.

47. The assembly of claim 36 wherein the working channel is attached to the body portion at a plurality of attachment points.

48. The assembly of claim 36 wherein the working channel is adapted to slideably receive at least a portion of a medical device having an operating end, the working channel comprising an enlarged end portion proximate an end of the body portion, the enlarged end portion being adapted to at least partially receive the operating end of the medical device.

49. The assembly of claim 36 wherein the working channel comprises a channel fabricated from a material selected from the group consisting of TEFLON®, urethane, polyvinyl chloride (PVC), acrylic, polycarbonate, and polyethylene terephthalate.

50. The assembly of claim 36 wherein the body portion includes an end cap adapted to encapsulate a working end of the insertion tube.

51. An endoscopic assembly, comprising:
an elongated insertion tube;
a sheath assembly including a body portion at least partially encapsulating the insertion tube; and
a working channel attached to the body portion and extending along at least a portion of the body portion, the working channel having a gap disposed therein, the gap being at least partially transverse to a longitudinal axis of the working channel, the gap being adapted to widen along at least a portion thereof when the working channel is subjected to an axial tension force.

52. The assembly of claim 51 wherein the gap comprises a spiral gap.

53. The assembly of claim 51 wherein the working channel further has a plurality of additional gaps disposed therein, the plurality of additional gaps being at least partially transverse to the longitudinal axis, the working channel being adapted to widen along at least a portion of at least some of the additional gaps when the working channel is subjected to the axial tension force.

54. The assembly of claim 51 wherein the working channel includes a first plurality of additional gaps disposed in a first side thereof and a second plurality of additional gaps disposed in a second side thereof, the additional gaps being at least partially transverse to the longitudinal axis, the working channel being adapted to widen along at least a portion of at least some of the additional gaps when the working channel is subjected to the axial tension force.

55. The assembly of claim 54 wherein the second side is substantially opposite from the first side.

56. The assembly of claim 54 wherein the additional gaps are uniformly disposed within the working channel.

57. The assembly of claim 54 wherein the additional gaps are non- uniformly disposed within the working channel.

58. The assembly of claim 51 wherein the gap extends along a portion of the working channel adapted to be approximately aligned with a bending section of the insertion tube.

59. The assembly of claim 51 wherein the working channel is attached to an outer surface of the body portion.

60. The assembly of claim 51 wherein the working channel extends along an inner surface of the body portion and is adapted to be positioned between the body portion and the insertion tube when the body portion is positioned to at least partially encapsulate the insertion tube.

61. The assembly of claim 51 wherein the gap being adapted to narrow along at least a portion thereof when the working channel is subjected to an axial compression force.

62. The assembly of claim 51 wherein the working channel is attached to the body portion at a plurality of attachment points.

63. The assembly of claim 51 wherein the working channel is adapted to slideably receive at least a portion of a medical device having an operating end, the working channel comprising an enlarged end portion proximate an end of the body portion, the enlarged end portion being adapted to at least partially receive the operating end of the medical device.

64. The assembly of claim 51, further comprising a headpiece attached to the insertion tube.

65. The assembly of claim 51 wherein the working channel comprises a channel fabricated from a material selected from the group consisting of TEFLON®, urethane, polyvinyl chloride (PVC), acrylic, polycarbonate, and polyethylene terephthalate.

66. The assembly of claim 51 wherein the body portion includes an end cap that encapsulates a working end of the insertion tube.

67. The assembly of claim 51 wherein the body portion includes a tubular portion that encapsulates a portion of the insertion tube, and an end cap that encapsulates a working end of the insertion tube, the tubular portion being axially stretched onto the insertion tube.

68. A method of performing a procedure using an endoscopic insertion tube, comprising:
providing a sheath assembly having a body portion that at least partially encapsulates the endoscopic insertion tube;
providing a working channel attached to the body portion and extending along at least a portion of the body portion, the working channel having a cut disposed therein, the cut being at least partially transverse to a longitudinal axis of the working channel, the working channel being separable along at least a portion of the cut when the working channel is subjected to an axial tension force; and
exerting an axial tension force on the working channel to separate the working channel along at least a portion of the cut.

69. The method of claim 68 wherein providing a working channel attached to the body portion comprises providing a working channel having a spiral cut disposed therein.

70. The method of claim 68 wherein providing a working channel attached to the body portion comprises providing a working channel having a plurality of additional cuts disposed therein, the plurality of additional cuts being at least partially transverse to the longitudinal axis, the working channel being separable along at least a portion of at least some of the plurality of additional cuts when the working channel is subjected to the axial tension force.

71. The method of claim 68 wherein providing a working channel attached to the body portion comprises providing a working channel having a cut that extends approximately perpendicularly to the longitudinal axis of the working channel disposed therein.

72. The method of claim 68 wherein providing a working channel attached to the body portion comprises providing a working channel having a cut that extends only partially through the working channel disposed therein.

73. The method of claim 68 wherein providing a working channel attached to the body portion comprises providing a working channel having a cut approximately aligned with a bending section of the insertion tube.

74. The method of claim 68 wherein providing a working channel attached to the body portion comprises providing a working channel attached to an outer surface of the body portion.

75. The method of claim 68 wherein providing a working channel attached to the body portion comprises providing a working channel that extends along an inner surface of the body portion adjacent the insertion tube.

76. The method of claim 68 wherein providing a working channel attached to the body portion comprises providing a working channel adapted to overlap along at least a second portion of the cut when the working channel is subjected to an axial compression force.

77. The method of claim 68 wherein exerting an axial tension force on the working channel comprises articulating a bending section of the insertion tube to apply the axial tension force on the working channel.

78. The method of claim 68 wherein exerting an axial tension force on the working channel comprises stretching the body portion of the sheath assembly onto the insertion tube to apply the axial tension force on the working channel.

79. The method of claim 68 further comprising exerting an axial compression force on the working channel to compress the working channel along at least a second portion of the cut.

80. The method of claim 68, further comprising inserting a medical device through the working channel.

81. The method of claim 68 wherein providing a working channel includes providing a working channel having an enlarged end portion, further comprising drawing a medical device into the enlarged end portion of working channel.

82. The method of claim 68 further comprising inserting the insertion tube into a patient.

83. A method of performing a procedure using an endoscopic insertion tube, comprising:
   providing a sheath assembly having a body portion that at least partially encapsulates the endoscopic insertion tube;
   providing a working channel attached to the body portion and extending along at least a portion of the body portion, the working channel having a gap disposed therein, the gap being at least partially transverse to a longitudinal axis of the working channel, the working channel being separable along at least a portion of the gap when the working channel is subjected to an axial tension force; and
   exerting an axial tension force on the working channel to separate the working channel along at least a portion of the gap.

84. The method of claim 83 wherein providing a working channel attached to the body portion comprises providing a working channel having a spiral gap disposed therein.

85. The method of claim 83 wherein providing a working channel attached to the body portion comprises providing a working channel having a gap approximately aligned with a bending section of the insertion tube.

86. The method of claim 83 wherein providing a working channel attached to the body portion comprises providing a working channel attached to an outer surface of the body portion.

87. The method of claim 83 wherein providing a working channel attached to the body portion comprises providing a working channel that extends along an inner surface of the body portion adjacent the insertion tube.

88. The method of claim 83 wherein providing a working channel attached to the body portion comprises providing a working channel adapted to overlap along at least a second portion of the gap when the working channel is subjected to an axial compression force.

89. The method of claim 83 wherein exerting an axial tension force on the working channel comprises articulating a bending section of the insertion tube to apply the axial tension force on the working channel.

90. The method of claim 83 wherein exerting an axial tension force on the working channel comprises stretching the body portion of the sheath assembly onto the insertion tube to apply the axial tension force on the working channel.

91. The method of claim 83 further comprising exerting an axial compression force on the working channel to compress the working channel along at least a second portion of the gap.

92. The method of claim 83 further comprising inserting a medical device through the working channel.

93. The method of claim 83 wherein providing a working channel includes providing a working channel having an enlarged end portion, further comprising drawing a medical device into the enlarged end portion of working channel.

94. The method of claim 83, further comprising inserting the insertion tube into a patient.

* * * * *